US007563777B2

(12) United States Patent
Laguens et al.

(10) Patent No.: US 7,563,777 B2
(45) Date of Patent: Jul. 21, 2009

(54) METHOD TO INDUCE NEOVASCULAR FORMATION AND TISSUE REGENERATION

(75) Inventors: Rubén Laguens, Buenos Aires (AR); Marcelo L. Argüelles, Buenos Aires (AR); Gustavo Leónidas Vera Janavel, Buenos Aires (AR); José Alberto Crottogini, Buenos Aires (AR); Carlos Alberto Melo, Buenos Aires (AR); Ricardo Horacio Pichel, Buenos Aires (AR); Marcelo Eduardo Criscuolo, Buenos Aires (AR)

(73) Assignees: Sterrenbeld Biotechnologie North America, Inc., Wilmington, DE (US); Fundacion Universitaria Dr. Rene G. Favaloro, Buenos Aires (AR)

( * ) Notice: Subject to any disclaimer, the term of this patent is extended or adjusted under 35 U.S.C. 154(b) by 448 days.

(21) Appl. No.: 10/714,449

(22) Filed: Nov. 17, 2003

(65) Prior Publication Data
US 2005/0020522 A1   Jan. 27, 2005

Related U.S. Application Data

(63) Continuation-in-part of application No. PCT/US02/14508, filed on May 13, 2002.

(30) Foreign Application Priority Data

May 15, 2001   (AR)   ............................. P010102313

(51) Int. Cl.
*A61K 31/70*   (2006.01)
*A61K 48/00*   (2006.01)
*A01N 63/00*   (2006.01)
*C12N 5/00*   (2006.01)
*C12N 15/00*   (2006.01)

(52) U.S. Cl. ................. 514/44; 424/93.1; 424/93.2; 435/320.1; 435/325; 435/455

(58) Field of Classification Search ................. None
See application file for complete search history.

(56) References Cited

U.S. PATENT DOCUMENTS 6,040,157 A   3/2000   Hu et al.

FOREIGN PATENT DOCUMENTS

| WO | WO-98/32859 | 7/1998 |
| WO | WO-00/04928 | 2/2000 |
| WO | WO-01/13031 | 2/2001 |

OTHER PUBLICATIONS

Vale et al. Circulation 102:965-974, 2000.*
Isner, Nature 415, 234-239, 2002.*
Kajstura et al, Proc Natl Acad Sci U S A. 95(15):8801-5, 1998.*
Goncalves, Bioessays. 27(5):506-517, 2005.*
Juengst, BMJ, 326:1410-11, 2003.*
Check NATURE 422:7, 2003.*
Couzin et al, SCIENCE 307:1028, 2005.*
Wolf, Nat. Biotechnol. 20, 768-769, 2002.*
Rosenberg et al, SCIENCE 287:1751, 2000.*
Touchette, Nat. Med. 2(1) 7-8, 1996.*
Carmeliet P. Mechanisms of angiogenesis and arteriogenesis. Nat Med. Apr. 2000; 6(4):389-95.
Braunwald E, Bristow MR. Congestive heart failure: fifty years of progress. Circulation. Nov. 14, 2000; 102(20 Suppl 4):IV14-23.
Ware A and Simons M (editors). Angiogenesis and Cardiovascular Disease (Oxford University Press Inc., New York, USA, 1999). pp. 159-198, Chapter 8.
Ware A and Simons M (editors). Angiogenesis and Cardiovascular Disease (Oxford University Press Inc., New York, USA, 1999). pp. 258-188, Chapter 12.
Lazarous DF et al., Comparative effects of basic fibroblast growth factor and vascular endothelial growth factor on coronary collateral development and the arterial response to injury. Circulation. Sep. 1, 1996; 94(5):1074-82.
Asahara T et al., Local delivery of vascular endothelial growth factor accelerates reendothelialization and attenuates intimal hyperplasia in balloon-injured rat carotid artery. Circulation. Jun. 1, 1995; 91(11):2793-801.
Banai S et al., Angiogenic-induced enhancement of collateral blood flow to ischemic myocardium by vascular endothelial growth factor in dogs. Circulation. May 1994; 89(5):2183-9.
Grosskreutz CL et al., Vascular endothelial growth factor-induced migration of vascular smooth muscle cells in vitro. Microvasc Res. Sep. 1999; 58(2):128-36.
Seko Y et al., Vascular endothelial growth factor (VEGF) activates Raf-1, mitogen-activated protein (MAP) kinases, and S6 kinase (p90rsk) in cultured rat cardiac myocytes. J Cell Physiol. Jun. 1998; 175(3):239-46.

(Continued)

*Primary Examiner*—Sumesh Kaushal
(74) *Attorney, Agent, or Firm*—Venable LLP; Nancy J. Axelrod; Michael A. Gollin

(57) ABSTRACT

The present invention relates, e.g., to a method for inducing arteriogenesis, lymphangiogenesis, vasculogenesis, or cardiomyogenesis, and/or for inducing mitosis or proliferation of a smooth muscle cell, a skeletal muscle cell, or a cardiomyocyte, comprising administering to a cell or tissue in need thereof a dose of a polynucleotide that encodes a vascular endothelial growth factor (VEGF), or that encodes a polypeptide comprising an active site of the VEGF. The coding sequence is operably linked to an expression control sequence; and the dose is sufficient to induce arteriogenesis, lymphangiogenesis, vasculogenesis, or cardiomyogenesis, and/or to induce mitosis or proliferation of a smooth muscle cell, a skeletal muscle cell, or a cardiomyocyte. In preferred embodiments of the invention, the method is a method of tissue regeneration, particularly of cardiomyogenesis; and the polynucleotide (or a polypeptide encoded by such a polynucleotide) is administered into the myocardium.

45 Claims, 13 Drawing Sheets

OTHER PUBLICATIONS

Takahashi N et al., Vascular endothelial growth factor induces activation and subcellular translocation of focal adhesion kinase (p125$^{FAK}$) in cultured rat cardiac myocytes. Circ Res. May 28, 1999; 84(10):1194-202.

Schaper W. Quo vadis collateral blood flow? A commentary on a highly cited paper. Cardiovasc Res. Jan. 1, 2000; 45(1):220-3.

Poltorak et al., VEGF $_{145}$, a Secreted Vascular Endothelial Growth Factor Isoform That Binds to Extracellular Matrix, The Journal of Biological Chemistry, Mar. 14, 1997, 272 (11): 7151-7158.

Vale PR, Losordo DW, Symes JF, Isner JM. Gene therapy for myocardial angiogenesis. Circulation 1998; (Suppl.I):I322 (Abstract #1687).

Losordo DW et al., Gene therapy for myocardial angiogenesis: initial clinical results with direct myocardial injection of phVEGF$_{165}$ as sole therapy for myocardial ischemia. Circulation. Dec. 22-29, 1998; 98(25):2800-4.

Symes JF et al., Gene therapy with vascular endothelial growth factor for inoperable coronary artery disease. Ann Thorac Surg. Sep. 1999; 68(3):830-6; discussion 836-7.

Murray et al., Mortality By Cause for Eight Regions Of The World: Global Burden Of Disease Study, May 3, 1997, The Lancet, vol. 349,: 1269-1276.

Reddy KS et al., Emerging epidemic of cardiovascular disease in developing countries. Circulation. Feb. 17, 1998; 97(6):596-601.

Henry TD. Therapeutic angiogenesis. BMJ. Jun. 5, 1999; 318(7197):1536-9.

Thomas KA. Vascular endothelial growth factor, a potent and selective angiogenic agent. J Biol Chem. Jan. 12, 1996; 271(2):603-6.

Leung DW, Cachianes G, Kuang WJ, Goeddel DV, Ferrara N. Vascular endothelial growth factor is a secreted angiogenic mitogen. Science. Dec. 8, 1989; 246(4935):1306-9.

Tischer E et al., The human gene for vascular endothelial growth factor. Multiple protein forms are encoded through alternative exon splicing. J Biol Chem. Jun. 25, 1991; 266(18):11947-54.

Ferrara N et al., The vascular endothelial growth factor family of polypeptides. J Cell Biochem. Nov. 1991; 47(3):211-8 (Abstract Only).

de Vries C et al., The fms-like tyrosine kinase, a receptor for vascular endothelial growth factor. Science. Feb. 21, 1992; 255(5047):989-91. (Abstract Only).

Terman BI et al., Identification of the KDR tyrosine kinase as a receptor for vascular endothelial cell growth factor. Biochem Biophys Res Commun. Sep. 30, 1992; 187(3):1579-86. (Abstract Only).

Galland F et al., Chromosomal localization of FLT4, a novel receptor-type tyrosine kinase gene. Genomics. Jun. 1992; 13(2):475-8. (Abstract Only).

Jakeman LB et al., Binding sites for vascular endothelial growth factor are localized on endothelial cells in adult rat tissues. J Clin Invest. Jan. 1992; 89(1):244-53. (Abstract Only).

Ferrara N et al., The biology of vascular endothelial growth factor. Endocr Rev. Feb. 1997; 18(1):4-25.

Guerrin M et al., Vasculotropin/vascular endothelial growth factor is an autocrine growth factor for human retinal pigment epithelial cells cultured in vitro. J Cell Physiol. Aug. 1995; 164(2):385-94. (Abstract Only).

Öberg-Welsh C et al., Effects of vasuclar endothelial growth factor on pancreatic duct cell replication and the insulin production of fetal islet-like cell clusters in vitro. Mol Cell Endocrinol. Feb. 7, 1997; 126(2):125-32.

Sondell M et al., Vascular endothelial growth factor has neurotrophic activity and stimulates axonal outgrowth, enhancing cell survival and Schwann cell proliferation in the peripheral nervous system. J Neurosci. Jul. 15, 1999; 19(14):5731-40.

Asahara T et al., Isolation of putative progenitor endothelial cells for angiogenesis. Science. Feb. 14, 1997; 275(5302):964-7.

Partanen TA et al., Endothelial growth factor receptor in human fetal heart. Circulation. Aug. 10, 1999; 100(6):583-6.

Safi J Jr et al., Gene therapy with angiogenic factors: a new potential approach to the treatment of ischemic diseases. J Mol Cell Cardiol. Sep. 1997; 29(9):2311-25.

Simons M et al., Clinical trials in coronary angiogenesis: issues, problems, consensus: An expert panel summary. Circulation. Sep. 12, 2000; 102(11):E73-86.

Takeshita S et al., Intramuscular administration of vascular endothelial growth factor induces dose-dependent collateral artery augmentation in a rabbit model of chronic limb ischemia. Circulation. Nov. 1994; 90(5 Pt 2):II228-34.

Henry TD et al., Results of intracoronary recombinant human vascular endothelial growth factor (rhVEGF) administration trial. J Am Coll Cardiol 31 (Suppl A): 65 A, 1998 (Abstract #810-1).

Horowitz JR et al., Vascular endothelial growth factor/vascular permeability factor produces nitric oxide-dependent hypotension. Evidence for a maintenance role in quiescent adult endothelium. Arterioscler Thromb Vasc Biol. Nov. 1997; 17(11):2793-800.

Lopez JJ et al., Hemodynamic effects of intracoronary VEGF delivery: evidence of tachyphylaxis and NO dependence of response. Am J Physiol. Sep. 1997; 273(3 Pt 2):H1317-23.

Mack CA et al., Biologic bypass with the use of adenovirus-mediated gene transfer of the complementary deoxyribonucleic acid for vascular endothelial growth factor 121 improves myocardial perfusion and function in the ischemic porcine heart. J Thorac Cardiovasc Surg. Jan. 1998; 115(1):168-76.

Tio RA et al., Intramyocardial gene therapy with naked DNA encoding vascular endothelial growth factor improves collateral flow to ischemic myocardium. Hum Gene Ther. Dec. 10, 1999; 10(18):2953-60.

Crystal RG. Transfer of genes to humans: early lessons and obstacles to success. Science. Oct. 20, 1995; 270(5235):404-10.

Magovern CJ et al., Direct in vivo gene transfer to canine myocardium using a replication-deficient adenovirus vector. Ann Thorac Surg. Aug. 1996; 62(2):425-33.

Wersto RP et al., Recombinant, replication-defective adenovirus gene transfer vectors induce cell cycle dysregulation and inappropriate expression of cyclin proteins. J Virol. Dec. 1998; 72(12):9491-502.

Walder CE et al., Vascular endothelial growth factor augments muscle blood flow and function in a rabbit model of chronic hindlimb ischemia. J Cardiovasc Pharmacol. Jan. 1996; 27(1):91-8. (Abstract Only).

Takeshita S et al., Gene transfer of naked DNA encoding for three isoforms of vascular endothelial growth factor stimulates collateral development in vivo. Lab Invest. Oct. 1996;75(4):487-501.

Mack CA et al., Salvage angiogenesis induced by adenovirus-mediated gene transfer of vascular endothelial growth factor protects against ischemic vascular occlusion. J Vasc Surg. Apr. 1998; 27(4):699-709.

Tsurumi Y et al., Direct intramuscular gene transfer of naked DNA encoding vascular endothelial growth factor augments collateral development and tissue perfusion. Circulation. Dec. 15, 1996; 94(12):3281-90.

Gilgenkrantz H et al., Transient expression of genes transferred in vivo into heart using first-generation adenoviral vectors: role of the immune response. Hum Gene Ther. Oct. 1995; 6(10):1265-74. (Abstract Only).

Dewey RA et al., Chronic brain inflammation and persistent herpes simplex virus 1 thymidine kinase expression in survivors of syngeneic glioma treated by adenovirus-mediated gene therapy: implications for clinical trials. Nat Med. Nov. 1999; 5(11):1256-63. (Abstract Only).

Zou Y et al., Leukemia inhibitory factor enhances survival of cardiomyocytes and induces regeneration of myocardium after myocardial infarction. Circulation. Aug. 12, 2003; 108(6):748-53.

Hollon T. Researchers and regulators reflect on first gene therapy death. Nat Med. Jan. 2000; 6(1):6.

Chan SY et al., Tissue-specific consequences of the anti-adenoviral immune response: implications for cardiac transplants. Nat Med. Oct. 1999;5(10):1143-9. (Abstract Only).

Byrnes AP et al., Immunological instability of persistent adenovirus vectors in the brain: peripheral exposure to vector leads to renewed inflammation, reduced gene expression, and demyelination. J Neurosci. May 1, 1996; 16(9):3045-55.

Folkman J. Angiogenesis in cancer, vascular, rheumatoid and other disease. Nat Med. Jan. 1995; 1(1):27-31.

Ferrara N. The role of vascular endothelial growth factor in pathological angiogenesis. Breast Cancer Res Treat. 1995; 36(2):127-37. (Abstract Only).

Aiello LP et al., Vascular endothelial growth factor in ocular fluid of patients with diabetic retinopathy and other retinal disorders. N Engl J Med. Dec. 1, 1994; 331(22):1480-7.

Adamis AP et al., Increased vascular endothelial growth factor levels in the vitreous of eyes with proliferative diabetic retinopathy. Am J Ophthalmol. Oct. 15, 1994; 118(4):445-50. (Abstract Only).

Inoue M et al., Vascular endothelial growth factor (VEGF) expression in human coronary atherosclerotic lesions: possible pathophysiological significance of VEGF in progression of atherosclerosis. Circulation. Nov. 17, 1998; 98(20):2108-16.

Bolognese L et al., Early predictors of left ventricular remodeling after acute myocardial infarction. Am Heart J. Aug. 1999; 138(2 Pt 2):S79-83.

Mehta RH et al., Current concepts in secondary prevention after acute myocardial infarction. Herz. Feb. 2000; 25(1):47-60. (Abstract Only).

Hessen SE et al., Risk profiling the patient after acute myocardial infarction. Cardiovasc Clin. 1989; 20(1):283-318. (Abstract Only).

Jacoby RM et al., Acute myocardial infarction in the diabetic patient: pathophysiology, clinical course and prognosis. J Am Coll Cardiol. Sep. 1992; 20(3):736-44. (Abstract Only).

Beltrami AP et al., Evidence that human cardiac myocytes divide after myocardial infarction. N Engl J Med. Jun. 7, 2001; 344(23):1750-7.

Kajstura J et al., Myocyte proliferation in end-stage cardiac failure in humans. Proc Natl Acad Sci U S A. Jul. 21, 1998; 95(15):8801-5.

Herget GW et al. DNA content, ploidy level and number of nuclei in the human heart after myocardial infarction. Cardiovasc Res. Oct. 1997; 36(1):45-51.

Dorfman J et al., Myocardial tissue engineering with autologous myoblast implantation. J Thorac Cardiovasc Surg. Nov. 1998; 116(5):744-51.

Murry CE et al., Skeletal myoblast transplantation for repair of myocardial necrosis. J Clin Invest. Dec. 1, 1996; 98(11):2512-23.

Leor J et al., Transplantation of fetal myocardial tissue into the infarcted myocardium of rat. A potential method for repair of infarcted myocardium? Circulation. Nov. 1, 1996; 94(9 Suppl):II332-6. (Abstract Only).

Li RK et al., In vivo survival and function of transplanted rat cardiomyocytes. Circ Res. Feb. 1996; 78(2):283-8. (Abstract Only).

Orlic D et al., Bone marrow cells regenerate infarcted myocardium. Nature. Apr. 5, 2001; 410(6829):701-5.

Kocher AA et al., Neovascularization of ischemic myocardium by human bone-marrow-derived angioblasts prevents cardiomyocyte apoptosis, reduces remodeling and improves cardiac function. Nat Med. Apr. 2001; 7(4):430-6.

Adler CP et al., Myocardial DNA content, ploidy level and cell number in geriatric hearts: post-mortem examinations of human myocardium in old age. J Mol Cell Cardiol. Jan. 1986; 18(1):39-53. (Abstract Only).

Schratzberger P et al., Reversal of experimental diabetic neuropathy by VEGF gene transfer. J Clin Invest. May 2001; 107(9):1083-92.

Rivard A et al., Rescue of diabetes-related impairment of angiogenesis by intramuscular gene therapy with adeno-VEGF. Am J Pathol. Feb. 1999; 154(2):355-63.

Anversa P et al., Loss of intermediate-sized coronary arteries and capillary proliferation after left ventricular failure in rats. Am J Physiol. May 1991; 260(5 Pt 2):H1552-60.

Adari TH et al., A stereological method for estimating length density of the arterial vascular system. Am J Physiol. Apr. 1994; 266(4 Pt 2):H1434-8.

Anversa P et al., Li P, Sonnenblick EH, Olivetti G. Effects of aging on quantitative structural properties of coronary vasculature and microvasculature in rats. Am J Physiol. Sep. 1994; 267(3 Pt 2):H1062-73.

Hamawy AH et al., Cardiac angiogenesis and gene therapy: a strategy for myocardial revascularization. Curr Opin Cardiol. Nov. 1999; 14(6):515-22.

Neufeld G et al., Vascular endothelial growth factor and its receptors. Prog Growth Factor Res. 1994; 5(1):89-97. (Abstract Only).

Olofsson B et al., Vascular endothelial growth factor B, a novel growth factor for endothelial cells. Proc Natl Acad Sci U S A. Mar. 19, 1996; 93(6):2576-81.

Chilov D et al., Genomic organization of human and mouse genes for vascular endothelial growth factor C. J Biol Chem. Oct. 3, 1997; 272(40):25176-83.

Olofsson B et al., Current biology of VEGF-B and VEGF-C. Curr Opin Biotechnol. Dec. 1999; 10(6):528-35.

Poltorak Z et al., Neufeld G. $VEGF_{145}$, a secreted vascular endothelial growth factor isoform that binds to extracellular matrix. J Biol Chem. Mar. 14, 1997; 272(11):7151-8.

Keck PJ et al., Vascular permeability factor, an endothelial cell mitogen related to PDGF. Science Dec. 8, 1989; 246(4935):1309-12.

Senger DR et al., Tumor cells secrete a vascular permeability factor that promotes accumulation of ascites fluid. Science. Feb. 25, 1983; 219(4587):983-5. (Abstract Only).

Brown DC et al., Monoclonal antibody Ki-67: its use in histopathology. Histopathology. Dec. 1990; 17(6):489-503. (Abstract Only).

Gerdes J et al., Cell cycle analysis of a cell proliferation-associated human nuclear antigen defined by the monoclonal antibody Ki-67. J Immunol. Oct. 1984; 133(4):1710-5. (Abstract Only).

Scholzen T et al., The Ki-67 protein: from the known and the unknown. J Cell Physiol. 2000; 182:311-322.

Soonpaa MH et al., Survey of studies examining mammalian cardiomyocyte DNA synthesis. Circ Res. Jul. 13, 1998; 83(1):15-26.

MacLellan RW et al., Genetic dissection of cardiac growth control pathways. Annu Rev Physiol. 2000; 62:289-320.

Anversa P et al., Ventricular myocytes are not terminally differentiated in the adult mammalian heart. Circ Res. Jul. 13, 1998; 83(1):1-14.

Anversa P et al., Myocyte renewal and ventricular remodelling. Nature. Jan. 10, 2002; 415(6868):240-3.

Limana F et al., bcl-2 overexpression promotes myocyte proliferation. Proc Natl Acad Sci U S A. Apr. 30, 2002; 99(9):6257-62.

Laguens R et al., Entrance in mitosis of adult cardiomyocytes in ischemic pig hearts after plasmid-mediated $rhVEGF_{165}$ gene transfer. Gene Ther. Dec. 2002; 9(24):1676-81.

Henry TD et al., Double blind, placebo controlled trial of recombinant human vascular endothelial growth factor—the VIVA trial. J Am Coll Cardiol Feb. 1999; 33(Suppl.A):384A (Abstract #874-4).

Henry TD et al., VIVA trial: one year follow up. Circulation 102 (Suppl II): II 309, 2000 (Abstract #1516).

Henry TD et al., The VIVA trial: Vascular endothelial growth factor in Ischemia for Vascular Angiogenesis. Circulation. Mar. 18, 2003; 107(10):1359-65.

Harada K et al., Vascular endothelial growth factor administration in chronic myocardial ischemia. Am J Physiol. May 1996; 270(5 Pt 2):H1791-802.

Ishida A et al., Expression of vascular endothelial growth factor receptors in smooth muscle cells. J Cell Physiol. Sep. 2001; 188(3):359-68.

Crottogini A et al., Arteriogenesis induced by intramyocardial vascular endothelial growth factor 165 gene transfer in chronically ischemic pigs. Hum Gene Ther. Sep. 20, 2003; 14(14):1307-18.

Sun Y et al., VEGF-induced neuroprotection, neurogenesis, and angiogenesis after focal cerebral ischemia. J Clin Invest. Jun. 2003; 111(12):1843-51.

Schwarz ER et al., Evaluation of the effects of intramyocardial injection of DNA expressing vascular endothelial growth factor (VEGF) in a myocardial infarction model in the rat—angiogenesis and angioma formation. J Am Coll Cardiol. Apr. 2000; 35(5):1323-30.

Kornowski R et al., Delivery strategies to achieve therapeutic myocardial angiogenesis. Circulation. Feb. 1, 2000; 101(4):454-8.

Robinson CJ et al., The splice variants of vascular endothelial growth factor (VEGF) and their receptors. J Cell Sci. Mar. 2001; 114(Pt 5):853-65.

Shibuya M. Structure and function of VEGF/VEGF-receptor system involved in angiogenesis. Cell Struct Funct. Feb. 2001; 26(1):25-35.

"Intramyocardial Gene Therapy with Naked DNA Encoding Vascular Endothelial Growth Factor Improves Collateral Flow to Ischemic Myocardium" by Rene A. Tio, et al., Human Gene Therapy 10:2953-2960 (Dec. 10, 1999) Mary Ann Liebert, Inc.

Losorso et al., "Gene Therapy for Myocardial Angiogenesis Initial Clinical Results with Direct Myocardial Injection of phVEGF$_{165}$ as Sole Therapy for Myocardial Ischemia", Circulation, American Heart Association, vol. 98, No. 25, 1998, pp. 2800-2804, XP000946361.

Takeshita et al., "Time Course of Increased Cellular Proliferation in Collateral Arteries After Administration of Vascular Endothelial Growth Factor in a Rabbit Model of Lower Limb Vascular Insufficiency", American Journal of Pathology, vol. 146, No. 6, 1995, pp. 1649-1660, XP009084496.

Supplementary European Search Report.

Kastrup et al., "*Direct Intramyocardial Plasmid Vascular Endothelial Growth Factor-A$_{165}$ Gene Therapy in Patients with Stable Severe Angina Pectoris*", JACC, 45(7), 2005, pp. 982-988.

Vera Janavel et al., "*Plasmid-mediated VEGF gene transfer induced cardiomyogenesis and reduces myocardial infarct size in sheep*", Gene Therapy, 2006, pp. 1-10.

Stewart/Cannon, "*Northern: A Prospective, Randomized, Double Blind, Placebo-Controlled Evaluation of Intramyocardian VEGF-165 Plasmid Gene Therapy in Patients with Refractory Angina*", Transcatheter Cardiovascular Therapeutics conference, Cardiovascular Research Foundation, Oct. 23, 2007, Abstract.

Lekas et al., *Growth factor-induced therapeutic neovascularization for ischaemic vascular disease: time for a re-evaluation*, Therapeutic neovascularization for ischaemic vascular disease, Current Opinion in Cardiology 21, pp. 376-383.

\* cited by examiner

METHOD TO INDUCE NEOVASCULAR FORMATION AND TISSUE REGENERATION

This application is a continuation-in-part of PCT/US02/14508, filed May 13, 2002, which is incorporated by reference herein in its entirety.

FIELD OF THE INVENTION

This invention relates, e.g., to a method for inducing arteriogenesis, lymphangiogenesis, vasculogenesis, or cardiomyogenesis, or for inducing mitosis or proliferation of a smooth muscle cell, a skeletal muscle cell, or a cardiomyocyte, using a Vascular Endothelial Growth Factor (VEGF). For example, a gene therapy method is described for in vivo localized induction of neovascular formation or tissue regeneration in mammals utilizing VEGF.

BACKGROUND OF THE INVENTION

Ischemic heart disease is the main cause of morbidity and mortality. The epidemiological and socio-economical impact of coronary heart disease is remarkable. This disease causes million of deaths all over the world. See Murray, et al., *Lancet,* 349:1269-1276 (1997). In developed countries, it has been estimated that 5.3 million deaths attributable to cardiovascular disease occurred in 1990, whereas the corresponding figure for the developing countries ranged between 8 to 9 million (showing a relative excess of 70%). See Reddy, et al., *Circulation,* 97:596-601 (1998). In Argentina, ischemic heart disease is the first cause of mortality showing an incidence of around 30%, trend which tends to remain stable since 1980. For the population over 65 years, this rate reaches almost 40%. See Programa Nacional de Estadisticas de Salud, Series 5, Number 38, Ministerio de Salud y Acción Social, República Argentina (December 1995).

Despite recent advances in prevention and treatment of ischemic heart disease, there are many patients who are still symptomatic and cannot benefit from conventional therapy. Administration of growth factors that promote neovascular formation and growth, such as fibroblast growth factors (FGFs) and VEGF, appear as a novel and promising alternative for these patients. This mode of treatment is called therapeutic angiogenesis. See Henry, *B. M. J.,* 318:1536-1539 (1999).

VEGF is a protein expressed by skeletal muscle cells, smooth muscle cells, ovarian corpus luteum cells, tumor cells, fibroblasts and cardiomyocytes. Unlike other mitogens, VEGF is a secreted growth factor. See Thomas, *J. Biol. Chem,* 271:603-606 (1996); Leung, et al., *Science,* 246:1306-1309 (1989). The human VEGF gene is expressed as different isoforms, secondary to post-transcriptional alternative splicing. In non-malignant human tissues, four VEGF isoforms are expressed, with different numbers of amino acids (121, 165, 189, 206) and with a molecular weight ranging from 34 to 46 kD. See Tischer, et al., *J. Biol. Chem.,* 266:11947-11954 (1991); Ferrara, et al., *J. Cell. Biochem.,* 47:211-218 (1991).

VEGF specific receptors are VEGFR-1 (flt-1), VEGFR-2 (KDR/flk-1) and VEGFR-3 (flt-4). See De Vries, et al., *Science,* 255:989-991 (1992); Terman, et al., *Biochem. Biophys. Res. Commun.,* 187:1579-1586 (1992); Gallant, et al., *Genomics,* 13:475-478 (1992). Due to the apparent restricted and confined localization of VEGF receptors to vascular endothelial cells, this growth factor has been described as the most specific mitogen for these cells. It has been proposed that VEGF is not bioactive on non-endothelial cells. See Jakeman, et al., *J. Clin. Invest.,* 89:244-253 (1992); Ferrara, et al., *Endocr. Rev.,* 18:4-25 (1997); Thomas, et al., supra (1996). However, recent studies have reported mitogenic effects of VEGF on some non-endothelial cell types, such as retinal pigment epithelial cells, pancreatic duct cells and Schwann cells. See Guerring et al., *J. Cell. Physiol.,* 164:385-394 (1995); Oberg-Welsh et al., *Mol. Cell. Endocrinol.,* 126:125-132 (1997); Sondell et al., *J. Neurosci.,* 19:5731-5740 (1999). Moreover, VEGF receptors have been found in other cells, such as hematopoietic stem cells, endocardial cells and even cultured rat cardiomyocytes, where VEGF has been shown to activate the mitogen-activated protein kinase cascade. See Asahara et al., *Science,* 275:964-967 (1997); Partanen et al., *Circulation,* 100:583-586 (1999); Takahashi et al., *Circ. Res.,* 84:1194-1202 (1999).

Therapeutic administration of VEGF is a significant challenge. VEGF can be administered as a recombinant protein (protein therapy) or by VEGF-encoding gene transfer (gene therapy). See Safi, et al., *J. Mol. Cell. Cardiol.,* 29:2311-2325 (1997); Simons, et al., *Circulation,* 102:E73-E86 (2000).

Protein therapy has several disadvantages. The extremely short mean-life of angiogenic proteins (e.g. VEGF) conditions therapy to the administration of high or repeated doses to achieve a noticeable effect. See Simons, et al., supra (2000); Takeshita, et al., *Circulation,* 90:II228-234 (1994). Furthermore, intravenous administration of high doses of VEGF protein is known to induce severe or refractory hypotension. See Henry, et al, J. Am. Coll. Cardiol., 31:65A (1998); Horowitz, et al., *Arterioscl. Thromb. Vasc. Biol.,* 17:2793-2800 (1997); López, et al., *Am. J. Phisiol.,* 273:H1317-1323 (1997). To avoid these disadvantages, gene therapy (e.g. DNA encoding for VEGF) has been proposed. See Mack, et al., *J. Thorac. Cardiovasc. Surg.,* 115:168-177 (1998); Tio, et al., *Hum. Gene Ther.,* 10:2953-2960 (1999).

Gene therapy can be compared to a drug slow-delivery system. The gene encoding for the agent of interest is transported into cells in vehicles called vectors (e.g. plasmids, viruses, liposomes). Cell mechanisms specialized in protein synthesis perform the production and localized release of the final product. See Crystal, *Science,* 270:404-410 (1995). In addition, it should be noted that in the case of plasmids the gene product is synthesized for a discrete period of time. This time is usually about two weeks. According to experimental studies, sustained expression during this limited period of time is necessary and sufficient to trigger the angiogenic process. Based on these advantages, several research groups have studied the therapeutic effects of gene therapy using angiogenic factors in experimental models of heart and limb ischemia. These approaches have yielded promising results. See Magovern, *Ann. Thorac. Surg.,* 62:425-434 (1996); Mack, et al., supra (1998); Tio, et al., supra (1999); Walder, et al., *J. Cardiovasc. Pharmacol.,* 27:91-98 (1996); Takeshita, et al., *Lab. Invest.,* 75:487-501 (1996); Mack, et al., *J. Vasc. Surg.,* 27:699-709 (1998); Tsurumi, et al., *Circulation,* 94:3281-3290 (1996). Gene therapy has achieved the expected effects without the shortcomings associated with protein therapy. However, adenoviral gene therapy may induce inflammatory or immune reactions, especially after repeated doses. This type of therapy has been related also to high risk systemic immune response syndrome. These circumstances limit significantly the clinical use of this therapy. See Gilgenkrantz, et al., *Hum. Gene Ther.,* 6:1265-1274 (1995); Dewey, et al., *Nat. Med.,* 5:1256-1263 (1999); Wersto, et al., *J. Virol.,* 72:9491-9502 (1998); Hollon, *Nat. Med.,* 6:6 (2000), Chan, et al., *Nat. Med.,* 5:1143-1149 (1999); Byrnes, et al., *J. Nerosci.,* 16:3045-3055 (1996). According to recent studies, plasmid gene therapy does not have these disadvantages and can be administrated safely in repeated doses. See Simons, et al., supra (2000).

Systemic administration of VEGF has been associated with undesired angiogenesis in peripheral tissues. See Folkman, *Nat. Med.*, 1:27-31 (1995); Liotta, et al., *Cell*, 64:327-336 (1991); Lazarous, et al., *Circulation*, 94:1074-1082 (1996); Ferrara, *Breast Cancer Res. Treat.*, 36:127-137 (1995); Ferrara, *Lab. Invest.*, 72:615-618 (1995); Aiello, et al., *N. Eng. J. Med.*, 331:1480-1485 (1994); Adams, et al., *Am. J. Ophthalmol.*, 118:445-450 (1994); Inoue, et al., *Circulation*, 98:2108-2116 (1998); Simons, et al., supra (2000). The risk of systemic exposure is probably more related to the route of administration than to the nature of therapy (gene or protein) utilized. In comparison with intravascular delivery, local (e.g. intramyocardial) administration reduces the risk of systemic exposure and undesired peripheral angiogenesis. See Simons, et al., supra (2000).

At the present, it has been demonstrated that VEGF induces angiogenesis in vivo. It has not been reported yet that VEGF induces the formation of blood vessels with a smooth muscle layer. See Mack, et al., supra (1998); Tio, et al., supra (1999). Moreover, it has been postulated that VEGF prevents the neoformation of vascular smooth muscle. See Asahara, et al., *Circulation*, 91:2793-2801 (1995). Smooth muscle plays a significant role in the regulation of vascular function. Its presence at the media layer of blood vessels represents an adaptative advantage since it is involved in the vasomotor tone regulation. Vascular smooth muscle maintains a basal vascular tone and permits self-regulation upon variations on blood flow and pressure. It has been suggested that the absence of smooth muscle layer is related to vessel collapse. See "Angiogenesis and Cardiovascular Disease", Ware, Ed. (Oxford University Press Inc., New York, USA., 1999), p. 258-261.

Acute myocardial infarction is the consequence of coronary heart disease with the worst short and long-term prognosis. See Bolognese, et al., *Am. Heart J.*, 138:S79-83 (1999); Mehta, et al., *Herz*, 25:47-60 (2000); Hessen, et al., *Cardiovasc. Clin.*, 20:283-318 (1989); Jacoby, et al., *J. Am. Coll. Cardiol.*, 20:736-744 (1992); Rosenthal, et al., *Am. Heart J.*, 109:865-876 (1985). This condition results frequently in a significant loss of myocardial cells, reducing the contractile muscle mass. It is known in the art that cardiomyocytes of human and human-like species preserve their ability to replicate DNA. See Pfizer, et al., *Curr. Top. Pathol.*, 54:125-168 (1971). Recently, it has been informed that some human cardiomyocytes can enter into M (mitotic) phase. However, this phenomenon occurs in a very small proportion of total cardiomyocyte population and under certain pathological conditions. So far, this phenomenon has only been noted in myocardial infarction and end-stage cardiac failure. See Beltrami et al., *N. Eng. J. Med.*, 344: 1750-1757 (2001); Kajstura, et al., *Proc. Natl. Acad. Sci. USA*, 95:8801-8805 (1998). There is no conclusive evidence in all these instances that cardiomyocytes divide into daughter cells.

The inability of cardiomyocytes to replicate properly precludes the replacement of myocardial tissue after injury in upper animal species. Under this scenario, myocardial function is diminished because the infarcted area is replaced by fibrotic tissue without contractile capacity. In addition, the remaining cardiomyocytes become hypertrophic and develop polyploid nuclei. See Herget, et al., *Cardiovasc. Res.* 36:45-51 (1997); "Textbook of Medical Physiology", 9th Ed., Guyton et al., Eds. (W. B. Saunders Co, USA, 1997).

Attempts have been made to restore myocardial cell loss with other cells, such as autologous satellite cells and allogenic myoblasts. The results of these attempts are not conclusive. See Dorfman, et al., *J. Thorac. Cardiovasc. Surg.*, 116:744-751 (1998); Murry, et al., *J. Clin. Invest.*, 98: 2512-2523 (1996); Leor, et al., *Circulation*, 94 Suppl.II: II-332-II-336 (1996); Li et al., *Circ. Res.*, 78:283-288 (1996). More recently, it has been suggested that pluripotent stem cells and bone marrow derived angioblasts might restore infarcted myocardial tissue and induce even neovascular formation. However, the efficiency of these methods in upper mammals has not been demonstrated yet. See Orlic, et al., *Nature*, 410:701-705 (2001); Kocher, et al., *Nat. Med.*, 7:430-436 (2001). An ideal method should induce cardiomyocyte division originating daughter cells and neovascular formation in myocardial tissue. This procedure would restore tissue loss with autologous myocardial tissue and increase simultaneously myocardial perfusion. A method like this would reduce the morbidity and mortality rates associated to left ventricular remodeling, myocardial infarction and ischemic heart disease. See Bolognese, et al., supra (1999).

Likewise, the failure of cardiomyocytes to replicate properly difficult adaptative hyperplasia (i.e. cell number increasing) as a response to other pathological conditions. In these cases, the adaptative response of human and porcine cardiomyocytes is to increase cell volume and nuclear DNA content. Therefore, in certain pathologies (e.g. hypertensive heart disease, dilated cardiomyopathy) cardiomyocytes are also markedly hypertrophic and polyploid. See Pfizer, *Curr. Top. Pathol.*, 54:125-168 (1971); Adler, et al., *J. Mol. Cell. Cardiol.*, 18:39-53 (1986). In most cases, cell adaptation is insufficient. Besides, the cellular demand for oxygen and nutrients increases as myocardial hypertrophy progresses. In consequence, the increased demands impair subendocardial perfusion even in the absence of coronary occlusion. Finally, the combination of these factors leads to myocardial function detriment. See "Textbook of Medical Physiology", $9^{th}$ Ed, supra. An ideal method should induce mitosis on hypertrophic and polyploid cells. This method should result in smaller and better-perfused daughter cells thus reducing the progression of cardiomyopathy towards heart failure.

BRIEF DESCRIPTION OF THE DRAWINGS

FIG. 6A shows Ki67-positive cardiomyocyte nuclei index. No significant differences exist between Group I-T (VEGF) and Group I-P (placebo) individuals. FIG. 6B shows Group I-T individuals (VEGF) with a significantly higher cardiomyocyte mitotic index for the area under risk (ischemic area) and the surrounding myocardial tissue (non-ischemic area) as compared with Group I-P individuals. The value for Group I-T (VEGF) is significantly higher than the value for Group I-P (placebo).

DESCRIPTION OF THE INVENTION

Figure 1:
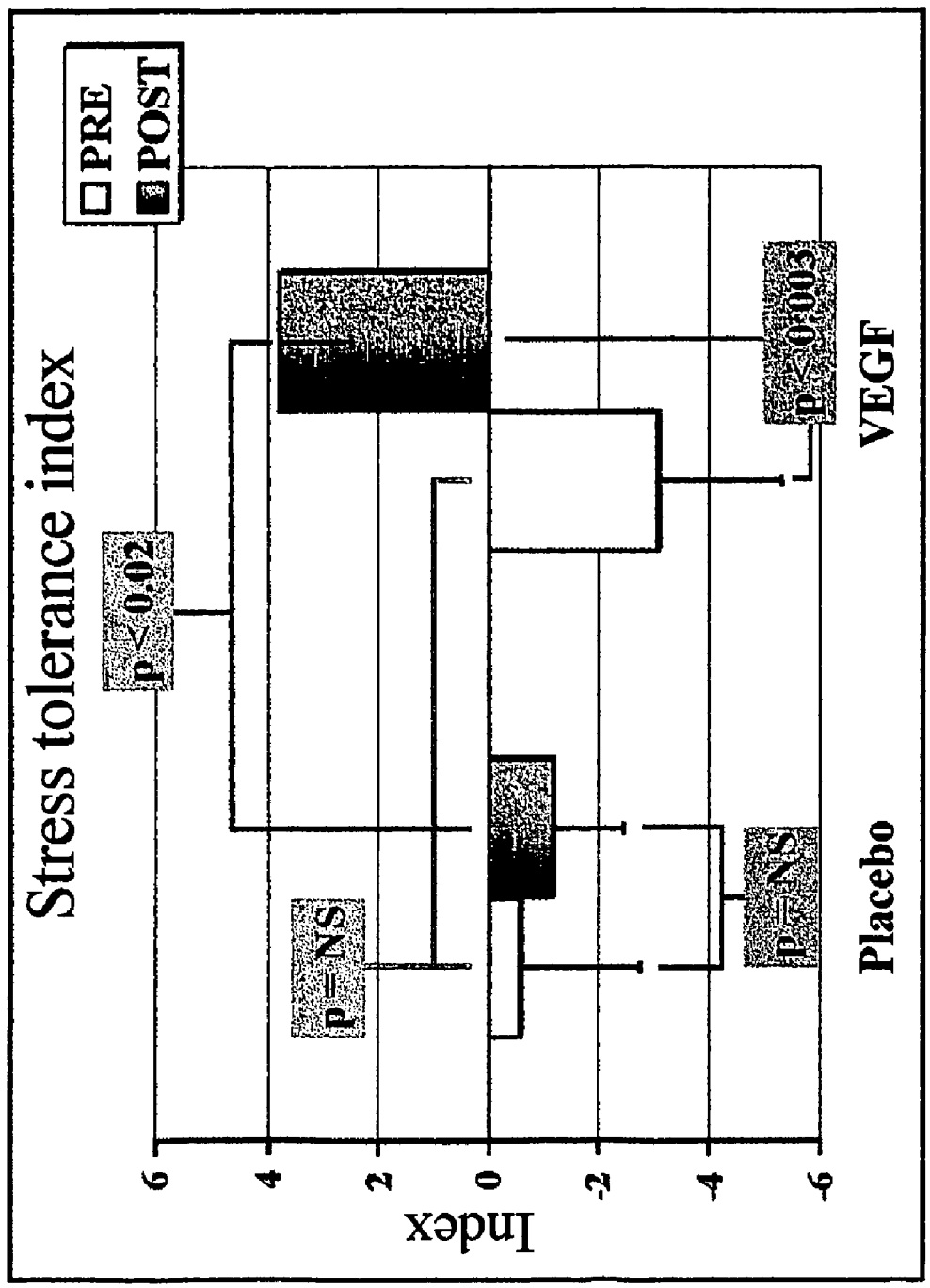
FIG. 1 illustrates the stress tolerance index for the area under risk. Pre and post-treatment mean values for Group I-T (VEGF) and Group I-P (placebo) are compared. The post-treatment value of Group I-T is higher to the pre-treatment value of the same group. The post-treatment value of Group I-T is higher the post-treatment value of Group I-P. Intra-group paired comparisons show: 1) absence of statistically significant differences between pre and post-treatment indexes for Group I-P and 2) presence of statistically significant differences between pre and post-treatment indexes for Group I-T. The non-paired comparisons between groups show: 1) absence of statistically significant differences between pre-treatment indexes for Group I-T and Group I-P and 2) presence of statistically significant differences between post-treatment indexes for Group I-T and Group I-P.

This invention relates, e.g., to a method for inducing arteriogenesis, lymphangiogenesis, vasculogenesis, or cardiomyogenesis, comprising administering to a cell or tissue in need thereof a dose of a polynucleotide that encodes a vascular endothelial growth factor (VEGF), or that encodes a polypeptide comprising an active site of the VEGF. In the method, the coding sequence is operably linked to an expression control sequence, and the dose is sufficient to induce arteriogenesis, lymphangiogenesis, vasculogenesis, or cardiomyogenesis. In a preferred embodiment, the VEGF is $VEGF_{1-165}$, whose amino acid sequence is represented by SEQ ID NO: 1.

The invention also relates to a method for inducing mitosis or proliferation of a smooth muscle cell, a skeletal muscle cell, or a cardiomyocyte, comprising administering to a cell in need thereof a dose of a polynucleotide that encodes a vascular endothelial growth factor (VEGF), or that encodes a polypeptide comprising an active site of the VEGF. In this method, the coding sequence is operably linked to an expression control sequence, and the dose is sufficient to induce the mitosis or proliferation. In a preferred embodiment, the VEGF is $VEGF_{1-165}$, whose amino acid sequence is represented by SEQ ID NO: 1. In some embodiments, the method is a method of tissue regeneration.

In preferred embodiments, the method of the invention is carried out in vivo, and a sufficient dose of the polynucleotide is administered to a subject in need of such treatment to induce arteriogenesis, lymphangiogenesis, vasculogenesis, or cardiomyogenesis, and/or to induce the mitosis or proliferation of a smooth muscle cell, a skeletal muscle cell, or a cardiomyocyte.

The invention also relates to a method for inducing arteriogenesis, lymphangiogenesis, vasculogenesis, or cardiomyogenesis, comprising administering to a cell or tissue in need thereof a dose of a VEGF polypeptide, or a polypeptide comprising an active site of the VEGF, the dose being sufficient to induce arteriogenesis, lymphangiogenesis, vasculogenesis, or cardiomyogenesis. The invention also relates to a method for inducing mitosis or proliferation of a smooth muscle cell, a skeletal muscle cell, or a cardiomyocyte, comprising administering to the cell a sufficient dose of a VEGF polypeptide, or a polypeptide that comprises an active site of the VEGF, to induce the mitosis or proliferation. In preferred embodiments, the VEGF is $VEGF_{1-165}$, whose amino acid sequence is represented by SEQ ID NO: 1.

The invention also relates to kits suitable for carrying out methods of the invention. In one embodiment, the kit comprises a polynucleotide or polypeptide of the invention and a label or instructions indicating a use for the polynucleotide or polypeptide to induce arteriogenesis, lymphangiogenesis, vasculogenesis, cardiomyogenesis, or to induce mitosis or proliferation of a smooth muscle cell, a skeletal muscle cell, or a cardiomyocyte. In another embodiment, the kit comprises a dose of a polynucleotide or polypeptide of the invention that is sufficient to induce mitosis or proliferation of a smooth muscle cell, a skeletal muscle cell, or a cardiomyocyte, and/or to induce the mitosis or proliferation of a smooth muscle cell, a skeletal muscle cell, or a cardiomyocyte.

The terms myocardiogenesis and cardiomyogenesis are understood by those in the art to be the same, and the terms are used interchangeably herein.

One advantage of the present invention is the secure and efficient induction of neovascular formation in hypoperfused and normoperfused tissues. By utilizing embodiments of the invention, it is possible, e.g., to stimulate the neoformation, development, proliferation and growth of vessels. Embodiments of the invention are effective also for the neoformation, development, proliferation and growth of smooth and striated muscular cells. The method is particularly useful for inducing revascularization in patients with ischemic heart disease. The present invention can also be used in the treatment of patients with peripheral artery disease or severe limb ischemia. The present invention can be utilized as sole therapy of ischemic diseases or associated with conventional revascularization procedures. The claimed method is characterized by the absence of adverse side effects related to the systemic exposure to angiogenic factors in high doses.

Another advantage of the present invention is the regeneration of myocardial tissue (myocardiogenesis). The claimed method includes the induction of cardiomyocyte mitosis and/or proliferation. In this way, the claimed method replaces infarcted tissue with autologous cardiac muscle. The present invention reverts also the natural development of hypertrophic and dilated cardiomyopathies of any etiology by inducing the mitotic process in polyploid hypertrophic cardiomyocytes and by improving tissue perfusion (i.e. inducing neovascular formation). This circumstance results in higher number of normal daughter cells. These daughter cells have a better perfusion compared to hypertrophic cells. All these advantages indicate that the present invention improves the short, mid and long-term clinical and histophysiological outcomes of heart disease.

Another potential advantage of this invention is its use in transplant medicine. The claimed invention may be particularly useful in transplanted patients with chronic graft rejection and diffuse coronary disease. The myocardial revascularization induced by the claimed method would restore the impaired perfusion and function in these patients. These patients are frequently not eligible for conventional revascularization methods (CABG, PTCA). The present invention represents an effective alternative revascularization strategy for these patients.

An additional potential advantage of the present invention is its use for increasing perfusion in ischemic tissues of patients with diabetes-related micro and macroangiopathy. The claimed method may revert or reduce chronic complications associated to diabetes such as diabetic neuropathy, vasa-vasorum disease, ischemic heart disease, peripheral artery disease and severe limb ischemia, among others. See Schratzberger, et al., *J. Clin. Invest.*, 107:1083-1092 (2001); Rivard, et al., *Circulation 96 Suppl I:* 175 (1997); Rivard, et al., *Am. J. Pathol.*, 154: 355-363 (1999).

One of the advantages of the claimed method is its high safety when used along with minimally invasive procedures of percutaneous intramyocardial-transendocardial administration. This administration can be achieved by accessing the left ventricular chamber through a catheter mediated endovascular approach. This type of administration may be assisted by fluoroscopy or an electromechanical mapping of the left ventricle. In this way the morbidity and mortality associated to open-chest surgery is significantly diminished.

In one embodiment of the invention, an inducing agent is administered to a cell, tissue, or subject in need thereof, wherein the inducing agent is a polynucleotide that encodes a VEGF and/or that encodes a polypeptide comprising an active site of the VEGF. As used herein, the singular forms "a", "an" and "the" include plural referents unless the context clearly dictates otherwise. For example, "an" active site, as used above, means one or more active sites. The VEGF polynucleotide may encode a full-length VEGF polypeptide; or it may encode a polypeptide consisting of one or more active sites of VEGF; or it may code a polypeptide consisting essentially of one or more active sites (e.g., sequences of intermediate length, which contain amino acids in addition to those of the active site, wherein the additional amino acids do not affect the basic and novel characteristics (e.g., activity) of the active site). In preferred embodiments, the VEGF is $VEGF_{1-165}$, whose amino acid sequence is represented by SEQ ID NO: 1.

A polynucleotide utilized according to the present invention may be, e.g., genomic DNA, cDNA or a messenger RNA. Preferably, the polynucleotide is a cDNA.

In preferred embodiments, a coding sequence as above is operably linked to an expression control sequence. As used herein, the term "expression control sequence" means a polynucleotide sequence that regulates expression of a polypeptide coded for by a polynucleotide to which it is functionally ("operably") linked. Expression can be regulated at the level of the mRNA or polypeptide. Thus, the term expression control sequence includes mRNA-related elements and protein-related elements. Such elements include promoters, domains within promoters, upstream elements, enhancers, elements that confer tissue or cell specificity, response elements, ribosome binding sequences, transcriptional terminators, etc. An expression control sequence is operably linked to a nucleotide sequence (e.g., a coding sequence) when the expression control sequence is positioned in such a manner to effect or achieve expression of the coding sequence. For example, when a promoter is operably linked 5' to a coding sequence, expression of the coding sequence is driven by the promoter. Suitable expression control sequences will be evident to the skilled worker.

Expression control sequences which can be used in methods of the invention, including both regulatable and constitutive control sequences, are well-known to those of skill in the art. Preferred expression control sequences are derived from highly-expressed genes, e.g., from genes encoding glycolytic enzymes such as 3-phosphoglycerate kinase (PGK), α-factor, acid phosphatase, or heat shock proteins, among others. Such expression control sequences can be selected from any desired gene, e.g using CAT (chloramphenicol transferase) vectors or other vectors with selectable markers. Particular named eukaryotic promoters include CMV immediate early, HSV thymidine kinase, early and late SV40, adenovirus promoters, LTRs from retrovirus, and mouse metallothionein-1. Selection of an appropriate vector and expression control sequence is well within the level of ordinary skill in the art.

In another embodiment of the invention, an inducing agent is administered to a cell, tissue, or subject in need thereof, wherein the inducing agent is a VEGF polypeptide, and/or a polypeptide comprising an active site of the VEGF. The VEGF may consist of, consist essentially of, or comprise, an active site of a VEGF. In a preferred embodiment, the VEGF is $VEGF_{1-165}$, whose amino acid sequence is represented by SEQ ID NO: 1.

According to the present invention, the inducing agent is administered to a eukaryotic cell or a tissue composed of eukaryotic cells, such as a mammalian cell or a tissue composed of mammalian cells. Preferably, mammalian cells are of porcine and human origin. More preferably, cells are of human origin.

In one embodiment, the eukaryotic cells are muscle cells. Preferably, the muscle cells are cardiomyocytes, skeletal myoblasts, skeletal striated muscle cells type I and type II, vascular smooth muscle cells or non-vascular smooth muscle cells or myoepithelial cells. More preferably, the muscle cells are cardiomyocytes.

One embodiment of the invention is the induction of neovascular formation. Preferably, the induced neovascular formation is localized in the site of administration of the inducing agent. More preferably, the site of administration is the myocardium.

Another embodiment of the invention is the induction of localized angiogenesis, either in vivo or ex vivo. Preferably, angiogenesis is localized at the administration site of the inducing agent. More preferably, the site of administration is the myocardium. In an embodiment of the present invention, angiogenesis is induced in normoperfused tissue, either in vivo, in vitro or ex vivo. In another embodiment of the present invention, angiogenesis is induced in ischemic tissue, either in vivo, in vitro or ex vivo. Preferably, the angiogenesis is induced in hypoperfused myocardial tissue, either in vivo, in vitro or ex vivo. Hypoperfused myocardial tissue may be ischemic, viable, hibernated, stunned, preconditioned, injured, infarcted, non-viable, fibrosed or necrosed. More preferably, the claimed method induces angiogenesis in vivo in hypoperfused myocardial tissue.

Another embodiment of the invention is the induction of arteriogenesis in vivo, in vitro or ex vivo. Preferably, arteriogenesis is localized at the site of administration. More preferably, the site of administration is the myocardium. In an embodiment of the present invention, arteriogenesis is induced in normoperfused tissue in vivo, in vitro or ex vivo. In another embodiment of the present invention, arteriogenesis is induced in ischemic tissue, in vivo, in vitro or ex vivo. Preferably, the arteriogenesis is induced in hypoperfused myocardial tissue in vivo, in vitro or ex vivo. Hypoperfused myocardial tissue may be ischemic, viable, hibernated, stunned, preconditioned, injured, infarcted, non-viable, fibrosed or necrosed. More preferably, the claimed method induces arteriogenesis in hypoperfused myocardial tissue in vivo.

Another embodiment of the invention is the induction of vasculogenesis in vivo, in vitro or ex vivo. Preferably, vasculogenesis is localized at the site of administration. More preferably, the site of administration is the myocardium. In an embodiment of the present invention, vasculogenesis is induced in normoperfused tissue in vivo, in vitro or ex vivo. In another embodiment of the present invention, vasculogenesis is induced in ischemic tissue, in vivo, in vitro or ex vivo. Preferably, the vasculogenesis is induced in hypoperfused myocardial tissue, in vivo, in vitro or ex vivo. Hypoperfused myocardial tissue may be ischemic, viable, hibernated, stunned, preconditioned, injured, non-viable, infarcted, necrosed or fibrosed. More preferably, the vasculogenesis is induced in hypoperfused myocardial tissue in vivo.

Another embodiment of the invention is the induction of lymphangiogenesis in vivo, in vitro or ex vivo. Preferably, lymphangiogenesis is localized at the site of administration. More preferably, the site of administration is the myocardium. In an embodiment of the present invention, lymphangiogenesis is induced in normoperfused tissue, in vivo, in vitro or ex vivo. In another embodiment of the present invention, lymphangiogenesis is induced in ischemic tissue, in vivo, in vitro or ex vivo. Preferably, the lymphangiogenesis is induced in hypoperfused myocardial tissue, in vivo, in vitro or ex vivo. Hypoperfused myocardial tissue may be ischemic, viable, hibernated, stunned, preconditioned, injured, non-viable, infarcted, necrosed or fibrosed. More preferably, the lymphangiogenesis is induced in hypoperfused myocardial tissue in vivo.

Another embodiment of the invention is the induction of mitosis in vivo, in vitro or ex vivo. Preferably, mitosis is induced locally at the site of administration. More preferably, the site of administration is the myocardium. In an embodiment of the present invention, mitosis is induced in normoperfused tissue, in vivo, in vitro or ex vivo. In another embodiment of the present invention, mitosis is induced in ischemic tissue in vivo, in vitro or ex vivo. Preferably, the mitosis is induced in hypoperfused myocardial tissue, in vivo, in vitro or ex vivo. Hypofused myocardial tissue may be ischemic, viable, hibernated, stunned, preconditioned, injured, non-viable, infarcted, necrosed or fibrosed. More preferably, the mitosis is induced in hypoperfused myocardial tissue in vivo.

The method also relates to the induction of proliferation of cells in which mitosis has been induced. In preferred embodiments, the mitosis or proliferation is in smooth muscle cells, skeletal muscle cells, or cardiomyocytes. In embodiments of the invention, a smooth muscle cell, skeletal muscle cell or cardiomyocyte in which mitosis or proliferation is induced is in myocardial tissue, skeletal tissue, or muscle tissue. Any type of muscle tissue may be regenerated by methods of the invention.

Another embodiment of the invention is the induction of tissue regeneration in vivo, in vitro or ex vivo. Preferably, tissue regeneration is induced locally at the site of administration. More preferably, the site of administration is the myocardium. In an embodiment of the present invention, tissue regeneration is induced in normoperfused territories, in vivo, in vitro or ex vivo. In another embodiment of the present invention, tissue regeneration is induced in ischemic territories, in vivo, in vitro or ex vivo. Preferably, the tissue regeneration is induced in hypoperfused myocardial territories, in vivo, in vitro or ex vivo. Hypoperfused myocardial territory may be ischemic, viable, hibernated, stunned, preconditioned, injured, non-viable, infarcted, necrosed or fibrosed. More preferably, the tissue regeneration is induced in hypoperfused myocardial territories in vivo.

In one embodiment of the present invention, the coding nucleotide sequence is inserted in a vector. In embodiments of the claimed method, the vector is a viral vector such as adenovirus, adeno-associated virus, retrovirus or lentivirus. In another embodiment of the present method, the vector is a plasmid vector. More preferably, the coding sequence inserted in a plasmid vector is pUVEK15.

Methods for inserting VEGF-coding sequences into vectors are conventional. Some suitable molecular biology methods, for use in these and other aspects of the invention, are provided e.g., in Sambrook, et al. (1989), *Molecular Cloning, a Laboratory Manual*, Cold Harbor Laboratory Press, Cold Spring Harbor, N.Y.; Ausubel et al. (1995). *Current Protocols in Molecular Biology*, N.Y., John Wiley & Sons; Davis et al. (1986), *Basic Methods in Molecular Biology*, Elseveir Sciences Publishing, Inc., New York; Hames et al. (1985), *Nucleic Acid Hybridization*, IL Press; Dracopoli et al. *Current Protocols in Human Genetics*, John Wiley & Sons, Inc.; and Coligan et al. *Current Protocols in Protein Science*, John Wiley & Sons, Inc.

In another embodiment of the present invention, the nucleotide sequence (e.g., when inserted into a plasmid vector) is transported by (administered to a cell or tissue by) a liposome. In an embodiment of the present invention, the inducing agent is in the form of a pharmaceutical composition. The pharmaceutical composition is administered to the recipient in sufficient doses.

A pharmaceutical composition used according to the present invention may be administered by intravenous, intracoronary, intra-aortic, intrafemoral, intrapopliteal, intrapedialis, intra-posterior tibialis, intracarotideal and intraradialis routes. The pharmaceutical compound may be also administered by intrapericardial, intra-amniotic sac, intrapleural, intramyocardial-transepicardial, intramyocardial-transendocardial, intra-peripheral muscle, subcutaneous, intraspinal, and intracardiac (intra-atrial and intraventricular) routes. In addition, the inducing agent may be administered by sublingual, inhalatory, oral, rectal, periadventitial, perivascular, topical epicardial, topical epidermal, transdermal, ophthalmic routes or through the conjunctival, nasopharyngeal, bucopharyngeal, laryngopharyngeal, vaginal, colonic, urethral and vesical mucoses. Preferably, the inducing agent is administered by intramyocardial-transepicardial or intramyocardial-transendocardial injections. More preferably, the inducing agent is administered by intramyocardial-transepicardial injection. In one embodiment of parenteral administration, the polynucleotide is administered in vehicles that are microbubbles, and the microbubbles are then disrupted by ultrasound directed at a site of interest, such that the polynucleotide is released at and introduced into the site of interest. The ultrasound treatment permits one to direct the release of the polynucleotide by disruption of the bubbles at the specific site at which the ultrasound is directed.

In an embodiment of the present invention, the inducing agent is injected perpendicular to the plane of injection area. In another embodiment of the present invention, the inducing agent is injected in parallel to the plane of the area of injection. In another embodiment of the present invention, the inducing agent is injected in an oblique angle in relation to the plane of the injection area. Preferably, the inducing agent is injected at an angle in relation to the plane of the injection area of between about 30 degrees and about 90 degrees. Injections may be homogeneously or heterogeneously distributed in the area of injection.

In a preferred embodiment, an inducing agent of the invention (polynucleotide or polypeptide) is formulated such that it is administered under slow-release conditions. Any repeated administration formulation or protocol may be used.

As used herein, "area of injection" includes the tissue territory including the hypoperfused area, the transition area and normoperfused area surrounding the transition area. "Area of injection" may also be defined as normal tissue.

As used herein, "area under risk" includes the myocardial area irrigated by the circumflex coronary artery.

As used herein, "arteriogenesis" includes the formation, growth or development of blood vessels with a smooth muscle media layer. Angiogenesis (of any thin-walled vessel that does not contain smooth muscle or a smooth muscle layer, e.g., a capillary vessel) is not encompassed by the term, arteriogenesis.

As used herein, "induce", as well as the correlated term "induction", refer to the action of generating, promoting, forming, regulating, activating, enhancing or accelerating a biological phenomenon. An example of induction is the action of VEGF as a vascular proliferation stimulator.

As used herein, "inducing agent" includes genomic DNA, cDNA or messenger RNA comprising sequences coding for the VEGF active site. "Inducing agent" also includes any vector containing a nucleotide sequence coding for VEGF. "Inducing agent" is also defined as any polypeptide including the VEGF active site.

As used herein, "Ki67-positive cardiomyocyte nuclei index" refers to a parameter designed to assess the density of cycling (non-quiescent) cells in a tissue sample. This parameter refers to the number of Ki67 positive cells per $10^6$ cardiomyocyte nuclei in an analyzed area.

As used herein, "length density index" refers to a parameter calculated for assessing a tissue vascularization. This parameter was designed to quantify vessels arranged in any variety of orientation. The method for calculating this index is known in the art. See Anversa et al., *Am. J. Physiol.*, 260. H1552-H1560 (1991); Adair et al., *Am. J. Physiol.*, 266: H1434-H1438 (1994); Anversa et al., *Am. J. Physiol.*, 267: H1062-H1073 (1994).

As used herein, "localized" is a response restricted to the area or tissue of interest.

As used herein, "lymphangiogenesis" includes the formation, growth, development or proliferation of lymphatic vessels.

As used herein, "mammal" includes a warm blooded vertebrate animal whose progeny feeds with milk secreted by its mammary glands. The term "mammal" includes, but is not limited to, rats, mice, rabbits, dogs, cats, goats, sheep, cows, pigs, primates and humans.

As used herein, "mitosis" refers to the complete cell division process.

As used herein, "mitotic index" refers to a parameter designed to assess the density of mitosis in a tissue sample. This parameter refers to the number of mitosis per $10^6$ cardiomyocyte nuclei in an analyzed area.

As used herein, "skeletal muscle cells" include striated muscle cells of muscle tissue and its precursors and progenitors, including skeletal myoblasts and skeletal muscle satellite cells.

As used herein, "neovascular formation" includes the creation, growth, development or proliferation of blood vessels.

Neovascular proliferation includes arteriogenesis, vasculogenesis and lymphangiogenesis.

As used herein, "non-paired comparison" refers to the statistical comparison between two different groups of individuals at the same time.

As used herein, "paired comparison" refers to the statistical comparison of the same group of individuals at different times.

As used herein, "perfusion improvement index" refers to a parameter designed to assess the overall improvement of left ventricular myocardial perfusion. This index is calculated by the arithmetical difference between the post-treatment stress tolerance index and the pre-treatment stress tolerance index.

As used herein, a "pharmaceutical composition" of the invention comprises a polynucleotide or polypeptide of the invention and a pharmaceutically acceptable carrier. The pharmaceutically acceptable carrier can be, e.g., a solvent, adjuvant or excipient used to administer an inducing agent. Pharmaceutical compositions can comprise any solvent, dispersion media, aqueous, gaseous solutions, antibacterial or antifungal agents, isotonic agents, either absorption delayer or accelerator agents, or similar substances. The use of said substances in the administration of pharmaceutically active compositions is known in the art. Supplementary active ingredients may also be incorporated to the pharmaceutical composition utilized in the present invention. Pharmaceutical compositions can comprise, but are not limited to, inert solid fillings or solvents, sterile aqueous solutions and non-toxic organic solvents. The pharmaceutically acceptable carrier should not react with or reduce in any other manner the efficiency or stability of the inducing agent. Pharmaceutically acceptable carriers include, but are not limited to, water, ethanol, polyethileneglycol, mineral oil, petrolatum, propyleneglycol, lanolin and similar agents. Pharmaceutical compositions for injection include sterile aqueous solutions (when soluble in water) or dispersions and sterile powders for extemporaneous preparation of sterile dispersions or injectable solutions. In all cases, the formulation should be sterile. The formulation may be fluid to facilitate syringe dispensation. The formulation should also be stable under manufacturing and storage conditions and should be preserved against the contaminant action of microorganisms such as bacteria, viruses and fungi.

As used herein, "post-treatment stress tolerance index" refers to a parameter designed to assess the left ventricular myocardial perfusion in post-treatment conditions. This index is calculated by the arithmetical difference between the post-treatment percentual perfusion value during pharmacological challenge (stress) and the post-treatment percentual perfusion value at rest.

As used herein, "pre-treatment stress tolerance index" refers to a parameter designed to assess the left ventricular myocardial perfusion in pre-treatment conditions. This index is calculated by the arithmetical difference between the pre-treatment percentual perfusion value during pharmacological challenge (stress) and the pre-treatment percentual perfusion value at rest.

As used herein, "stress tolerance index" is defined as the arithmetical difference between the percentual perfusion value during pharmacological challenge (stress) and the percentual perfusion value at rest. This index is calculated in post-treatment and pre-treatment situations.

In preferred embodiments, a method of the invention is carried out in vivo. A sufficient dose of an inducing agent (e.g., a polynucleotide or polypeptide of the invention) is administered to a subject (e.g., a patient) in need of such treatment. A subject "in need of such treatment" can be, e.g., a subject who exhibits signs or symptoms of, or who is suffering from, one of the mentioned conditions. "Signs" of a condition are manifestations assessed by physical examination, EKG or other methods, which are not full-fledged symptoms, but which are recognizable by a physician. For example, the subject may exhibit signs or symptoms of, or may suffer from, myocardial infarction, myocardial ischemia, dilated cardiomyopathy, or hypertrophic cardiomyopathy. Preferably, the subject is a human patient.

As used herein, a "sufficient dose" is a quantity of the inducing agent, or of a pharmaceutical composition including the inducing agent, which is adequate to attain at least a detectable amount of the specified function. In the context of the present invention, "sufficient dose" refers to a quantity of the inducing agent, or of the pharmaceutical composition including the inducing agent, which is adequate to produce, e.g., one or more of the following results: 1) the induction of arteriogenesis, vasculogenesis, lymphangiogenesis, or myocardiogenesis in eukaryotic cells, 2) the activation of the cell cycle in eukaryotic cells, 3) the induction or acceleration of the mitotic process in eukaryotic cells, e.g. the induction of mitosis or proliferation of a smooth muscle cell, a skeletal muscle cell, or a cardiomyocyte.

The sufficient dose for any particular use will vary from subject to subject, depending on, i.a., the species, age, weight and general or clinical condition of the subject, the severity or mechanism of any disorder being treated, the particular agent or vehicle used, the method and scheduling of administration, and the like. A therapeutically sufficient dose can be determined empirically, by conventional procedures known to those of skill in the art. See, e.g., *The Pharmacological Basis of Therapeutics*, Goodman and Gilman, eds., Macmillan Publishing Co., New York. For example, a sufficient dose can be estimated initially either in cell culture assays or in suitable animal models. The animal model may also be used to determine the appropriate concentration ranges and routes of administration. Such information can then be used to determine useful doses and routes for administration in humans. For example, the doses administered to pigs in the Examples herein can be converted to suitable doses for humans. A sufficient dose can also be selected by analogy to doses for comparable therapeutic agents.

In general, sufficient doses of VEGF-encoding polynucleotides vary from between about 0.003 to about 0.36 nmoles/kg body weight, depending on the route of administration and other factors as noted above. In a preferred embodiment, the dose is between about 0.01 and about 0.10 nmoles/kg. The nmoles are of polynucleotide encoding an active VEGF polypeptide. As used herein, an "active VEGF polypeptide" is a polypeptide that comprises an active site of a VEGF polypeptide, e.g., full-length VEGF or an active site thereof. The dose may be administered as a single dose, or in multiple doses (e.g., two or more doses) over an empirically determined amount of time. For example, the dose may be administered in two or more events, at different times, such as two or more weeks apart.

For polynucleotides in adenoviral viral vectors, a sufficient dose may vary between about $2.5 \times 10^{10}$ and about $10 \times 10^{15}$ pfu (plaque forming units), more preferably between about $3 \times 10^{10}$ and about $10 \times 10^{12}$ pfu. Comparable doses for other viral vectors will be evident to the skilled worker.

In general, it is preferable to formulate a polynucleotide of the invention in as concentrated a solution as possible. For example, in one embodiment of the invention, in which the polynucleotide coding sequence is inserted in a vector to form the plasmid, pUVEK15$^{VEGF}$, a concentration of between about 0.5 to about 4 mg/mL of the plasmid is preferred. Comparable concentrations of other vectors containing the coding sequences, or of polypeptides, will be evident to the skilled worker.

In general, sufficient doses of VEGF polypeptides vary from between about 0.35 and about 3.5 mg/kg body weight, depending on the route of administration and other factors as noted above. In a preferred embodiment, the dose is between about 0.4 and about 1.4 mg/kg. The mgrams are of active VEGF polypeptide. The dose may be administered as a single dose, or in multiple doses (e.g., two or more doses) over an empirically determined amount of time.

As used herein, "vasculogenesis" includes the formation, growth, development or proliferation of blood vessels derived from undifferentiated or underdifferentiated cells.

As used herein, "VEGF" includes any vascular endothelial growth factor. "VEGF" includes, but is not limited to, the VEGF variants A, B, C, D, E and F. See Hamawy, et al., *Curr. Opin. Cardiol.*, 14:515-522 (1999); Neufeld, et al., *Prog. Growth Factor Res.*, 5:89-97 (1994); Olofsson, et al., *Proc. Natl. Acad. Sci. USA*, 93:2576-2581 (1996); Chilov, et al., *J. Biol. Chem.*, 272:25176-25183 (1997); Olofsson, et al., *Curr. Opin. Biotechnol.*, 10:528-535 (1999). The VEGF A variant includes, but is not limited to, isoforms $VEGF_{1-121}$, $VEGF_{1-145}$, $VEGF_{1-167}$, $VEGF_{1-165}$, $VEGF_{1-189}$ and $VEGF_{1-206}$. The SEQ ID NO. 1 illustrates an example of isoform $VEGF_{1-165}$. See Tischer, et al., *J. Biol. Chem.*, 266: 11947-11954 (1991); Poltorak, et al., *J. Biol. Chem.*, 272: 7151-7158 (1997). The term "VEGF" also includes the vascular permeability factor or vasculotropin (VPF). See Keck, et al., *Science* 246:1309-1312 (1989); Senger, et al., *Science*, 219:983-985 (1983). VPF is currently known in the art as VEGF A. Other members of the VEGF family can also be used, including placental growth factors PlGF I and II.

The sequences of suitable VEGFs are readily available, e.g., on the web site of the National Center for Biotechnology Information (NCBI). For example, the loci for human VEGF family members include: VEGF-A-P15692 and NP003367; VEGF-B-NP003368, P49765, AAL79001, AAL79000, AAC50721, AAB06274, and AAH08818; VEGF-C-NP005420, P49767, S69207, AAB36425, and CAA63907; VEGF-D-NP004460, AAH27948, 043915, CAA03942 and BAA24264; VEGF-E-AAQ88857; VEGF-F-2VPFF; PlGF-1-NP002623, AAH07789, AAH07255, AAH01422, P49763, CAA38698 and CAA70463; synthetic constructs of Chain A-1FZVA and Chain B-1FZVB of PlGF-1; and PlGF-2-AAB25832 and AAB30462.

In preferred embodiments, the VEGF is of human origin. However, VEGF from other species, such as mouse, may also be used.

Structure/function analysis has identified a number of sequences and amino acid residues of VEGF that are important for its activity. Thus, it would be evident to a skilled worker which residues constitute an "active site" for any particular VEGF activity. A review of some of the structure/function studies follows:

In the 1980s VEGF was identified independently as vascular permeability factor (VPF) and as vascular endothelial cell-specific growth factor (Senger 1983, Leung 1989). Molecular cloning of the genes encoding these "two" proteins clarified that they are essentially the same protein encoded by a single gene (VEGF gene). Therefore, this protein is referred to as VEGF, VEGF/VPF or, sometimes, as VPF.

X-ray crystallography of a VEGF fragment (residues 8-109) showed that VEGF belongs to the dimeric cysteine-knot growth factor superfamily (Muller 1997). Each monomer is characterized by an intra-chain disulphide bonded knot motif at one end of a four-stranded β sheet (Mc Donald 1993, Murray-Rust 1993, Sun 1995). One subdivision of this superfamily is the PDGF (platelet-derived growth factor) gene family, to which VEGF belongs. Among these gene products, 8 cysteine residues are conserved at the same positions, and these products function as a dimer form, since 2 out of 8 cysteines generate intermolecular cross-linking (S—S bonds motif). The other 6 cysteines make 3 intramolecular S—S bonds to form 3 loop structures (Wiesmann 1997). The monomers are held in a "side-by-side" orientation, the two β sheets lying perpendicular to the twofold-symmetry axis. The structure of the VEGF165 heparin-binding region (residues 111-165) has been solved separately by NMR and represents a novel type of heparin-binding domain (Fairbrother 1998).

All VEGF isoforms are secreted as covalently linked homodimers. Monomers associate initially through hydrophobic interactions and are then stabilized by disulphide bonding between Cys51 of one chain and Cys61 of the other (Pötgens 1994). The signal peptide (exon 1 and four residues of exon 2), which includes an amphipathic α-helix (residues 12-19) essential for this dimerization, is cleaved off during secretion (Leung 1989, Keck 1989, Siemeister 1998a). A potential N-glycosylation site exists at Asn74 and apparently has no effect on VEGF function but is required for efficient secretion (Peretz 1992, Claffey 1995). And it is important to remark that the secretion process is necessary for at least some of the VEGF biological activities (that depend on VEGF binding to other cells receptors).

Pötgens et al. showed that covalent dimerization of VEGF is essential for effective receptor binding and biological activity (Pötgens 1994). They found that VEGF mutants lacking cysteine residue 2 or 4 (directly involved in anti-parallel interchain disulphide bonds) competed poorly for receptor binding of labeled VEGF and had low biological activity, thus VEGF needs to be a covalent dimer for efficient receptor binding and activation. Furthermore, they also found that cysteine residue 5 was essential for VEGF dimerization and activity, while the mutant lacking cysteine residue 3 was only mildly affected in its ability to dimerize and had partial biological activity (Pötgens 1994).

Alanine-scanning analysis was performed to identify a positively charged surface in VEGF that mediates receptor binding (Ferrara 1997). Site-directed mutagenesis identified three acidic residues (Asp63, Glu64 and Glu67) in exon 3, and three basic residues (Arg82, Lys84 and His86) in exon 4 that are essential for binding to VEGF receptors VEGFR-1 and VEGFR-2, respectively. The most significant effect on endothelial cell proliferation was observed with mutations in the 82-86 region (Ferrara 1997, Key 1996a). Three highly flexible loops are clustered at each pole of VEGF at the dimer interface. Loop II contains the VEGFR-1 binding determinants and lies close to loop III of the opposing monomer, which binds to VEGFR-2 (Keyt 1996a). The positioning of these receptor-binding interfaces at each pole of VEGF seems to facilitate receptor dimerisation, which is essential for transphosphorylation and signalling, because mutant dimers that have only one receptor-binding site antagonize native VEGF activity (Siemeister 1998b).

The binding sites to extracellular matrix (ECM) seem to be also important for VEGF action. VEGF isoforms in the ECM constitute a reservoir of growth factor that can be slowly released by exposure to heparin, heparan sulphate and heparinases or more rapidly mobilized by specific proteolytic enzymes such as plasmin and urokinase-type plasminogen activator uPA (Houck 1992, Plouet 1997). These enzymes already contribute to vascular proliferation through ECM depolymerization and, as well as releasing sequestered VEGF from the cell surface and ECM, might also regulate VEGF bioactivity. Keyt et al. found that the removal of the carboxyl-terminal domain of VEGF165 is associated with a significant loss in bioactivity (Keyt 1996b).

Other relevant issues are the VEGF mediated synthesis or secretion of other growth factors or VEGF interaction with different mitogens to achieve the biological effects. For example VEGF has been shown to upregulate PDGF-BB (Hirschi 1998). Other example is the sequence encoded by exon 6 (not present in VEGF165) has also been shown to release bioactive bFGF from the ECM and cell surface and thus confers the ability to exert some of VEGF biological effects through bFGF signalling pathways (Jonca 1997)

A VEGF polypeptide used in methods of the invention may be a fragment or variant of a naturally occurring VEGF polypeptide, provided that the fragment or variant retains an activity of the naturally occurring polypeptide which allows it to achieve a result of a method of the invention. Such a fragment or variant is referred to herein as an "active fragment" or "active variant."

An active fragment of a VEGF polypeptide may be of any size that is compatible with the invention, e.g., a polypeptide that is shorter than a naturally occurring VEGF, but that retains an active site of the VEGF.

An active variant of a VEGF polypeptide may be, e.g., (i) one in which one or more of the amino acid residues are substituted with a conserved or non-conserved amino acid residue (preferably a conserved amino acid residue), which substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which additional amino acids are fused to the polypeptide, such as a leader or secretory sequence or a sequence which is employed for purification of the polypeptide, commonly for the purpose of creating a genetically engineered form of the protein that is susceptible to secretion from a cell, such as a transformed cell. The additional amino acids may be from a heterologous source, or may be endogenous to the natural gene. Examples of all of these types of variants will be evident to a skilled worker. Among the preferred modifications are glycosylation or PEGylation of the protein, and/or amino acid substitutions, which increase bioavailaility, biological activity, biological effect, and/or half-life of the protein.

The invention also encompasses active fragments or variants of naturally occurring polynucleotides encoding VEGF. Such an active fragment or variant retains an activity of the naturally occurring polynucleotide which allows it to achieve a result of a method of the invention. Suitable variant polynucleotides include polynucleotides that encode any of the fragments or variant polypeptides noted above. Also included are variants which reflect the degeneracy of the genetic code, or which are naturally occurring or artificially generated allelic variants of a wild type polynucleotide.

Active variant polynucleotides of the invention may take a variety of forms, including, e.g., naturally or non-naturally occurring polymorphisms, including single nucleotide polymorphisms (SNPs), allelic variants, and mutants. They may comprise, e.g., one or more additions, insertions, deletions, substitutions, transitions, transversions, inversions, chromosomal translocations, variants resulting from alternative splicing events, or the like, or any combinations thereof.

Other types of active variants will be evident to one of skill in the art. For example, the nucleotides of a polynucleotide can be joined via various known linkages, e.g., ester, sulfamate, sulfamide, phosphorothioate, phosphoramidate, methylphosphonate, carbamate, etc., depending on the desired purpose, e.g., improved in vivo stability, etc. See, e.g., U.S. Pat. No. 5,378,825. Any desired nucleotide or nucleotide analog can be incorporated, e.g., 6-mercaptoguanine, 8-oxoguanine, etc.

Active variant polynucleotides or polypeptides of the invention include polynucleotides or polypeptides having sequences that exhibit a percent identity to one of the sequences noted above of at least about 70%, preferably at least about 80%, more preferably at least about 90% or 95%, or 98%, provided that the polypeptide or polypeptide exhibits the desired function noted above.

Methods of determining the degree of identity of two sequences are conventional. The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Among suitable mathematical algorithms that can be used are those described in Karlin et al. (1993) Proc. Natl. Acad. Sci. USA 90:5873-5877; those of the GAP program I the GCG software package (Devereux et al. (1984) Nucleic Acids Res. 12 (1):387); and the algorithm of Myers and Miller, CABIOS (1989).

Alternatively, a suitable variant polynucleotide is one that hybridizes under standard conditions of high stringency to a naturally occurring VEGF-encoding polynucleotide.

As used herein, "underdifferentiated cells" are cells with a characteristic phenotypic profile but with the capacity of originating cells with a different phenotypic profile. "Underdifferentiated cells" include, but are not limited to, fibroblasts, myoblasts, osteoblasts, endothelial precursor cells, skeletal muscle satellite cells, neural tissue glial cells, stem cells, cardiac progenitor cells, and cardiac precursor cells.

In one embodiment, the present invention employs a plasmid called pUVEK15 of approximately 3086 base pairs (bp). The pUVEK15 plasmid is characterized by including a cytomegalovirus (CMV) promoter, a chimeric intron, a DNA fragment containing a vascular endothelial growth factor (VEGF)-encoding sequence and a DNA sequence of approximately 1290 bp, which confers resistance to kanamicyn. The VEGF nucleotide sequence present in the pUVEK15 plasmid encodes the human 165 amino acid VEGF polypeptide represented by SEQ ID NO: 1. The pUVEK15 plasmid is deposited under the access number DSM 13833 at DSMZ—Deutsche Sammlung von Mikroorganismen und Zellkulturen, Federal Republic of Germany.

Another embodiment of the invention is a kit suitable for carrying out a method of the invention. For example, the kit may comprise (a) a polynucleotide that encodes a vascular endothelial growth factor (VEGF), or that encodes a polypeptide comprising an active site of the VEGF, wherein the coding sequence is operably linked to an expression control sequence, and (b) a label or instructions indicating a use for the polynucleotide to induce arteriogenesis, lymphangiogenesis, vasculogenesis, myocardiogenesis, or mitosis or proliferation of a smooth muscle cell, a skeletal muscle cell, or a cardiomyocyte.

In another embodiment, the kit comprises a dose of a polynucleotide that encodes a vascular endothelial growth factor (VEGF), or that encodes a polypeptide encoding an active site of the VEGF, wherein the coding sequence is operably linked to an expression control sequence, the dose being sufficient to induce arteriogenesis, lymphangiogenesis, vasculogenesis, myocardiogenesis, or mitosis or proliferation of a smooth muscle cell, a skeletal muscle cell, or a cardiomyocyte.

In another embodiment, the kit comprises (a) a VEGF polypeptide, or a polypeptide the comprises an active site of the VEGF, and (b) a label or instructions indicating a use for the polypeptide to induce arteriogenesis, lymphangiogenesis, vasculogenesis, or myocardiogenesis, or mitosis or proliferation of a smooth muscle cell, a skeletal muscle cell, or a cardiomyocyte.

In another embodiment, the kit comprises a dose of a VEGf polypeptide, or a polypeptide that comprises an active site of the VEGF, the dose being sufficient to induce arteriogenesis, lymphangiogenesis, vasculogenesis, myocardiogenesis, or mitosis or to induce proliferation of a smooth muscle cell, a skeletal muscle cell, or a cardiomyocyte.

The reagents of a kit of the invention may be in containers in which the reagents are stable, e.g., in lyophilized form or stabilized liquids. The reagents may also be in single use form, e.g., in single dosage form.

Having described the invention in general terms, it will be more easily understood by reference to the following examples which are presented as an illustration and are not intended to limit the present invention, save when specifically indicated.

EXAMPLES

Example I

Induction of Ischemia

Eighty Landrace pigs weighing approximately 25 kg (approx. 3 months of age) were submitted to the following protocol: 1) each individual underwent clinical and laboratory assessment of good health; 2) a sterile thoracotomy was performed at the $4^{th}$ left intercostal space under general anesthesia (induction: thiopental sodium 20 mg/kg; maintenance: 2% enflurane) and the circumflex coronary artery was dissected free from surrounding tissue at its proximal portion; 3) an Ameroid constrictor was placed embracing the origin of the circumflex coronary artery; and 4) the thoracotomy was repaired.

Example II

Basal Pre-Treatment Studies

Three weeks after the first surgery indicated in the previous example, basal (pre-treatment) studies were performed on the individuals. The studies were conducted under sedation with sufficient doses of intravenous sodium thiopental and under electrocardiographic control. Basal myocardial perfusion studies were performed on each individual. The left ventricular perfusion was quantified by single photon emission computed tomography (SPECT) utilizing an ADAC Vertex Dual Detector Camera System (ADAC Healthcare Information Systems Inc., USA). Sestamibi marked with $^{99m}$Tc was utilized as contrast.

The studies were performed at rest and under pharmacological challenge with progressive doses of intravenous dobutamine. The dobutamine infusion was interrupted when heart rate was at least a 50% above the basal (rest) values.

Individuals fulfilling the inclusion criterium (hipoperfusion in a territory consistent with the circumflex coronary artery bed) were selected. Of the subjects considered, twenty six individuals developed chronic myocardial ischemia and were selected as satisfying the inclusion criterium.

Example III

Administration of VEGF Plasmid and Placebo Plasmid

The twenty six individuals of the previous example were distributed in two groups: A first group consisting of 16 individuals (Group I) and a second group consisting of 10 individuals (Group II). Group I individuals were utilized to perform histopathological and physiological studies. Group II individuals were utilized to assess the presence and expression of the VEGF plasmid.

Group I individuals were randomized into two subgroups (Group I-T and Group I-P) with the same number of members (4 females and 4 males per subgroup). The treated group was designated Group I-T. The placebo group was designated Group I-P.

Group II individuals were randomized into two subgroups (Group II-T and Group II-P). Eight individuals were allocated to Group II-T. Two individuals were allocated to Group II-P. The treated group was designated Group II-T. The placebo group was designated Group II-P.

A sterile reopening of the previous thoracotomy was performed each individual of both Group I and Group II (reoperation) under general anesthesia (induction: sodium thiopental 20 mg/kg, maintenance: 2% enflurane).

Each individual from Groups I-T and II-T received 10 injections of a solution containing pUVEK15 plasmid encoding for vascular endothelial growth factor (1.9 mg of pUVEK15 in 1 mL of saline). Each injection contained 200 µl of the plasmid solution. Each individual received a total dose of 3.8 mg of the pUVEK15 plasmid.

Each individual from Groups I-P and II-P received 10 injections of a solution containing $pUVEK15^{-VEGF}$ plasmid without the encoding region for the vascular endothelial growth factor (1.9 mg of $pUVEK15^{-VEGF}$ in 1 mL of saline). Each injection contained 200 µl of the plasmid solution. Each individual received a total dose of 3.8 mg of the $pUVEK15^{-}$$_{VEGF}$ plasmid.

Each aliquot was injected intramyocardically, starting from the normoperfused left anterior descending artery territory (2-3 aliquots) and spanning the basal and mid zones of the anterolateral left ventricular wall. The area of injection included the hypoperfused zone, the transition zone and the normoperfused tissue immediately surrounding the transition zone. The injections were administered at a 45 degree angle in relation to the plane of the myocardium area, avoiding intraventricular administration of the solution. The injections were homogeneously distributed in the area of injection. The thoracotomy was repaired in each individual after administration.

Example IV

Post-Treatment Studies

1. Histopathological and Physiological Studies

Five weeks after the second surgery (reoperation), post-treatment studies were performed on Group I individuals. The individual were sedated with sufficient doses of intravenous sodium thiopental. The left ventricular perfusion was assessed for each individual following the protocol described in example 2.

The individuals were euthanized using an overdose of thiopental sodium followed by a lethal injection of potassium chloride. The heart, kidneys, liver, lungs, skeletal muscle, eyes and gonads were excised for histopathological assessment, including neoangiogenesis and mitosis determinations. The histopathological studies were performed in myocardial and peripheral tissues according to the following protocols.

For myocardial studies, the pericardium, adherent fat, atria and right ventricular free wall were removed. In each animal, the left circumflex coronary artery was examined at the site of the Ameroid to assess for occlusion. Subsequently, the left ventricle, including the septum, was cut transversally at one third of the distance between the apex and the mitral annulus. Subsequently, a slice of 5 mm in thickness was cut from the distal end of the upper third, rinsed in Ringer solution and fixed flat for 48 hours in 10% formaldehyde buffered solution. This slice was chosen in order to: 1) limit the analysis to areas clearly perfused by only one vessel (left anterior descending coronary artery, left circumflex coronary artery or right coronary artery), without mixed supply from more than one artery, and 2) match the histology with the perfusion data.

After fixation, the slice was divided into 6 blocks, corresponding, from 1 to 6 to: the posterior half of the septum, the posterior wall, the posterolateral wall, the lateral wall, the anterior wall and the anterior half of the septum. These 6 blocks were embedded in Histowax™, and sections of 5 µm thickness were mounted on slides previously wetted in a 0.01% polylysine aqueous solution (Sigma Chemical Co., U.S.A.) and dried at 37° C. The sections were stained with hematoxylin-eosin. Identification of intramyocardial vessels was made under optical microscopy. The endothelium was identified by immunohistochemistry employing the biotin streptavidin technique and a monoclonal antibody against von Willebrand factor. The smooth muscle layer was identified by immunohistochemistry to assess arteriogenesis. A monoclonal antibody against alpha-actin (Biogenex Labs. Inc., U.S.A.) was utilized to this purpose.

For quantitative analysis of collateral circulation a digital analysis system was employed (Vidas Kontron, Germany). The analysis focused on arteriole-sized vessels (ranging from 8 to 50 µm of maximum diameter) with smooth muscle layer. The morphometric study was performed on the total slice area. The numerical and length density of collateral vessels were determined. The numerical density was calculated as number of collaterals (n) per square millimeter ($n/mm^2$). The collateral length density (Lc) was calculated with the methodology known in the art for vessels arranged in any variety of orientation. See Anversa et al., *Am. J. Physiol.,* 260: H1552-H1560 (1991); Adair et al., *Am. J. Physiol.,* 266: H1434-H1438 (1994); Anversa et al., *Am. J. Physiol.,* 267: H1062-H1073 (1994). For n vessels encountered in an area A, Lc, expressed in millimeters per unit volume of myocardium ($mm/mm^3$), is equal to the sum of the ratio R of the long to the short axis of each vessel.

$$Lc = 1/A \sum_{i=1}^{n} R_i = (R_1 + R_2 + R_3 + ... R_n)/A$$

In addition, the length density for intramyocardial vessels ranging from 8 to 30 µm of maximum diameter was also analyzed.

Both indexes (numerical and length density) were averaged for both the ischemic (posterolateral, lateral, and anterolateral walls) and the non-ischemic (septum, anterior and posterior walls) zones.

To evidence cardiomyocytes undergoing cell cycle and mitosis, two double immunohistochemical techniques were used in the tissue sections of the Group I individuals. The following protocols were performed:

(a) Tissue sections were incubated with a monoclonal antibody against the Ki67 antigen (Novocastra Labs., U.K.). The Ki67 is a protein expressed exclusively during the cell cycle which identifies nuclei undergoing the G1, S and G2-M phases and decorates condensed mitotic chromosomes. The Ki67 expression pattern is not affected by DNA damage or by apoptosis. See Brown et al., *Histopathology*, 17:489-503 (1990); Gerdes et al., *J. Immunol.*, 133:1710-1715 (1984); Ross et al., *J. Clin. Pathol.*, 48:M113-117 (1995). Subsequently, the sections were post-treated with a biotinilated anti-mouse immunoglobulin antiserum (Biogenex, USA), followed by peroxidase-labeled avidin and revealed with AEC as chromogen. Afterwards, the sections were incubated with an anti-sarcomeric α-actin antibody (Dako, USA) to identify striated muscular cells. Subsequently, the sections were post-treated with the biotinilated antiserum followed by alkaline phosphatase-labeled streptavidin (Biogenex, USA) and Fast Red as chromogen.

(b) Tissue sections were incubated with a monoclonal antibody against the Ki67 antigen (Novocastra Labs., U.K.). The sections were post-treated with biotinilated antibodies, and revealed with fluorescein-labeled streptavidin (Vector, USA). Afterwards, the sections were incubated with rhodamine-labeled phalloidin (Sigma, USA), a protein binding F-actin, in order to identify striated muscular cells.

The tissue sections treated with enzyme-labeled avidin were examined with light microscopy with Nomarski optics. The tissue sections stained with fluorescent reactants were examined with confocal microscopy (Zeiss, Federal Republic of Germany).

Cardiomyocyte nuclei (CMN) density (CMN per $mm^2$) was determined by counting the number of CMN in longitudinally oriented cells containing sarcomeric α-actin in a 5 $mm^2$ area of the lateral wall mesocardium. The number of Ki67-positive CMN and the number of cardiomyocyte mitosis were determined in the whole ventricular tissue section area of each individual (total scanned area, TSA). The TSA of the Group I individuals averaged $1345.7 \pm 289.7$ $mm^2$.

The Ki67-positive CMN index was calculated as: [Ki67-positive nuclei/(TSA×CMN density)]×$10^6$. The mitotic index was calculated as: [mitosis/(TSA×CMN density)]×$10^6$. Data was expressed as number of Ki67-positive nuclei and number of cardiomyocyte mitosis per $10^6$ CMN. Both indexes were averaged for both the ischemic (posterolateral, lateral, and anterolateral walls) and the non-ischemic (septum, anterior and posterior walls) zones for each individual.

For peripheral studies, the tissues were fixed in 10% formaldehyde buffered solution, sectioned in blocks and included in Histowax™ paraffin. Tissue slices of 5 μm thickness were obtained from the blocks and stained with hematoxylin-eosin. An histopathological assessment for possible toxic effects in remote tissues was made by optical microscopy.

2. Presence and Transcription of VEGF Plasmid in Myocardial Tissue

After the second surgery (reoperation) the Group II individuals were euthanized using an overdose of thiopental sodium followed by a lethal injection of potassium chloride, according to the following chronogram: 2 individuals from Group II-T after 3 days of reoperation, 2 individuals from Group II-T and 2 individuals from Group II-P after 10 days of reoperation, 2 individuals of Group II-T after 16 days of reoperation and 2 individuals from Group II-T after 35 days of reoperation. Necropsies were performed in each euthanized individual. Myocardial tissue of the area under risk was obtained from each individual.

The molecular assessment was performed to detect the presence of plasmidic DNA and its transcript (mRNA). The presence of plasmidic DNA and mRNA were determined by the polymerase chain reaction (PCR) and the reverse transcriptase-polymerase chain reaction (RT-PCR) techniques, respectively. See Mullis, et al., *Meth. Enzymol.*, 55:335-350 (1987); Belyavsky, et al., *Nucleic. Acids Res.*, 17:2919-2932 (1989).

Total RNA was isolated from tissue samples using Trizol reagent (Gibco BRL Life Technologies, USA) and treated with DNAse I (Promega, USA). RNA was quantified by spectrophotometry at $A_{260/280}$ nm. One μg of total RNA was reverse transcripted using random hexamers (PerkinElmer, USA). Human VEGF was then amplified from cDNA using Taq polymerase (PerkinElmer, USA) with the oligonucleotide primers 5'CAACATCACCATGCAGATT3' and 5'GCAGGAATTCATCGATTCA3' at cycling conditions of 95° C. for 15 sec, 52° C. for 30 sec and 65° C. for 30 sec, for 35 cycles. Non-competitive amplification of constitutive GAPDH was used to demonstrate the presence of intact mRNA in each total RNA sample. RT-PCR was performed in myocardial tissue of Group II-T individuals without reverse transcriptase to assess the possible contamination with plasmidic DNA or genomic DNA. The results of this control reaction were negative, excluding the possibility of contamination.

Example V

Results

1. Histopathological and Physiological Analysis

The perfusion and histopathological studies showed vascular formation and growth in myocardial tissue of treated individuals. The histopathological study also revealed the induction of mitosis in cardiomyocytes, endothelial cells and smooth muscle cells of Group I-T individuals.

The stress tolerance index and perfusion improvement index were determined for each myocardial segment of all Group I individuals in order to assess left ventricular perfusion. Mean values of both indexes were calculated for the area under risk and the surrounding tissue for each individual. Finally, the mean values for each group were calculated.

The analysis of the perfusion in the area under risk revealed that:

(a) Group I-P: absence of statistically significant differences between the pre-treatment and post-treatment stress tolerance indexes (intra-group paired comparison). This result indicates that the perfusion and stress tolerance did not improve in the Group I-P individuals after the placebo treatment.

(b) Group I-T: presence of statistically significant differences between the pre-treatment and post-treatment stress tolerance indexes (intra-group paired comparison). The post-treatment mean value was significantly higher than the pre-treatment mean value. This result indicates that the perfusion and stress tolerance improved significantly in the Group I-T individuals after pUVEK15 treatment.

(c) Pre-treatment stress tolerance indexes: absence of statistically significant differences between the pre-treatment mean values of Group I-T individuals and Group I-P individuals (inter-group non-paired comparison). This result demonstrates that perfusion was homogenous for both subgroups before treatment.

(d) Post-treatment stress tolerance indexes: presence of statistically significant differences between the post-treatment mean values of Group I-T individuals and Group I-P individuals (inter-group non-paired comparison). The post-treatment mean value of Group I-T was significantly higher than the post-treatment mean value of Group I-P. This result indicates that the perfusion and stress tolerance of Group I-T individuals were higher than the Group I-P individuals after treatment with pUVEK15.

(e) Perfusion improvement indexes: presence of statistically significant differences between both subgroups. The mean value for Group I-T individuals was significantly higher than the mean value for Group I-P individuals (inter-group non-paired comparison). This result indicates that the perfusion of the Group I-T individuals improved noticeably in comparison to the perfusion of the Group I-P individuals. Moreover, the perfusion in Group I-P individuals showed a trend to deterioration.

Figure 2:
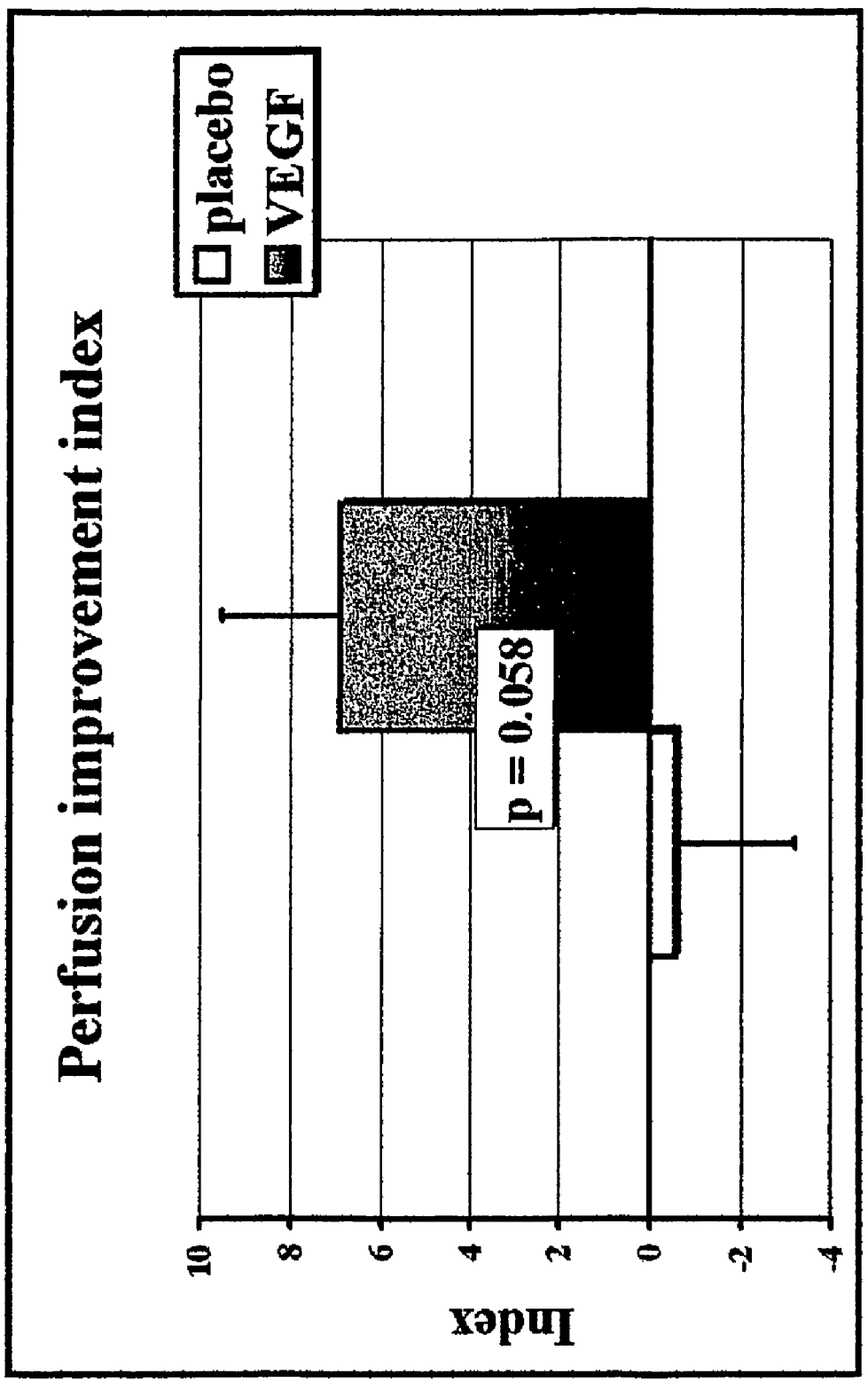
FIG. 2 illustrates the perfusion improvement index for the area under risk. Mean values for Group I-T (VEGF) and Group I-P (placebo) are compared. The value for Group I-T is significantly higher than the value for Group I-P.
Figure 3:
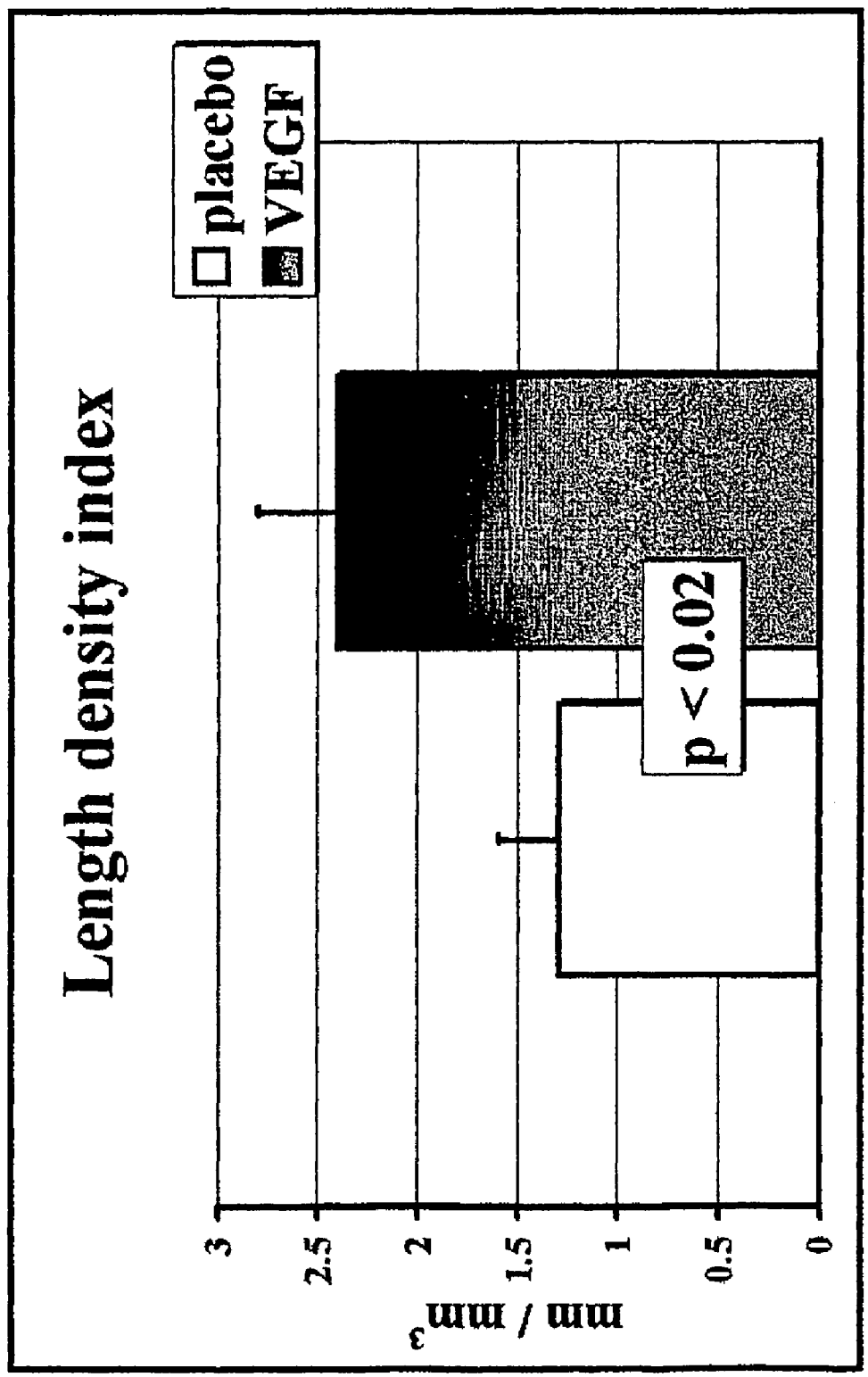
FIG. 3 shows the length density for the area under risk. Mean values for blood vessels with smooth muscle layer ranging from 8 to 50 μm are illustrated. The value for Group I-T (VEGF) is significantly higher than the value for Group I-P (placebo).
Figure 4:
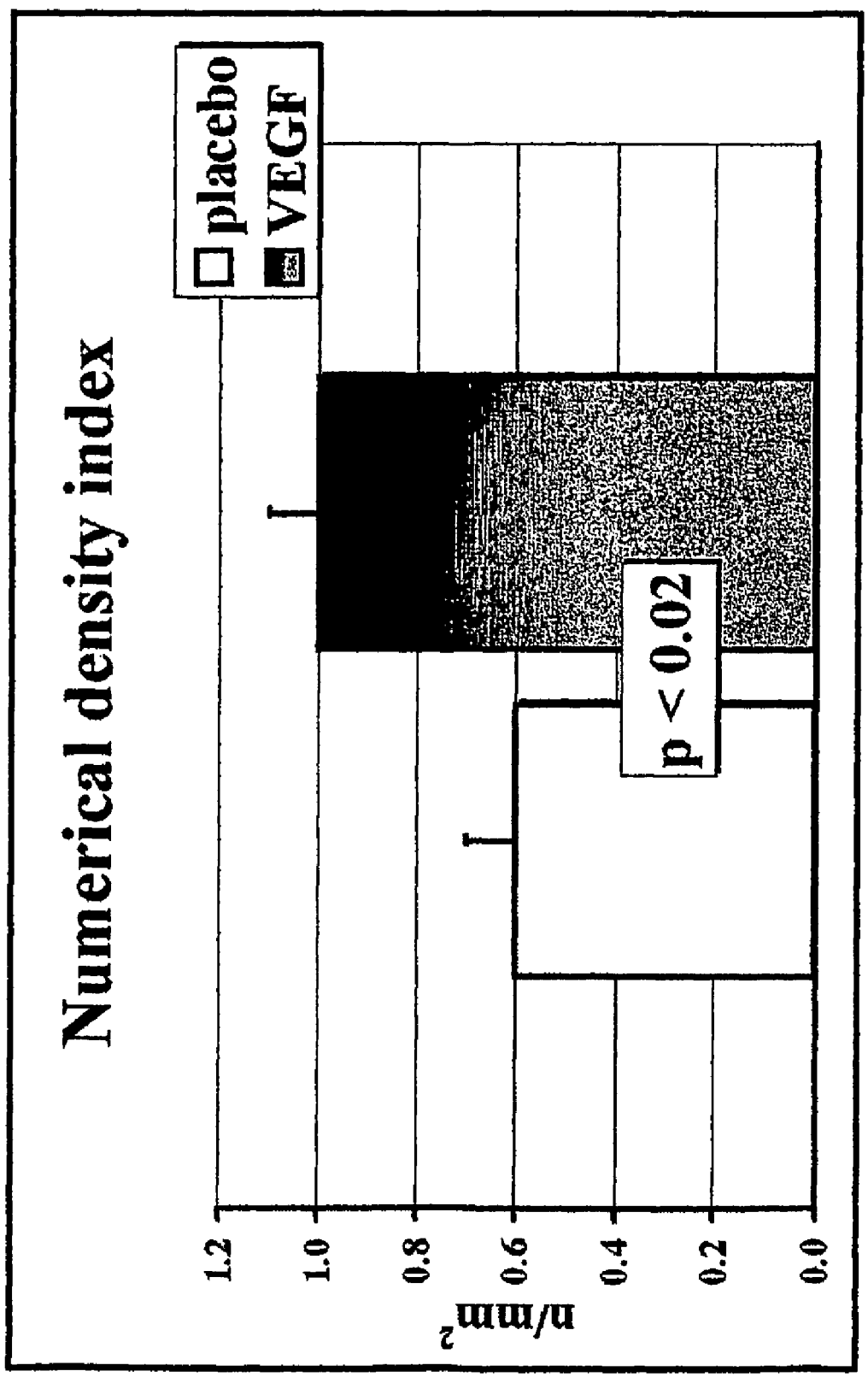
FIG. 4 shows the numerical density for the area under risk. Mean values for blood vessels with smooth muscle layer ranging from 8 to 50 μm are illustrated. The value for Group I-T (VEGF) is significantly higher than the value for Group I-P (placebo).
Figure 5:
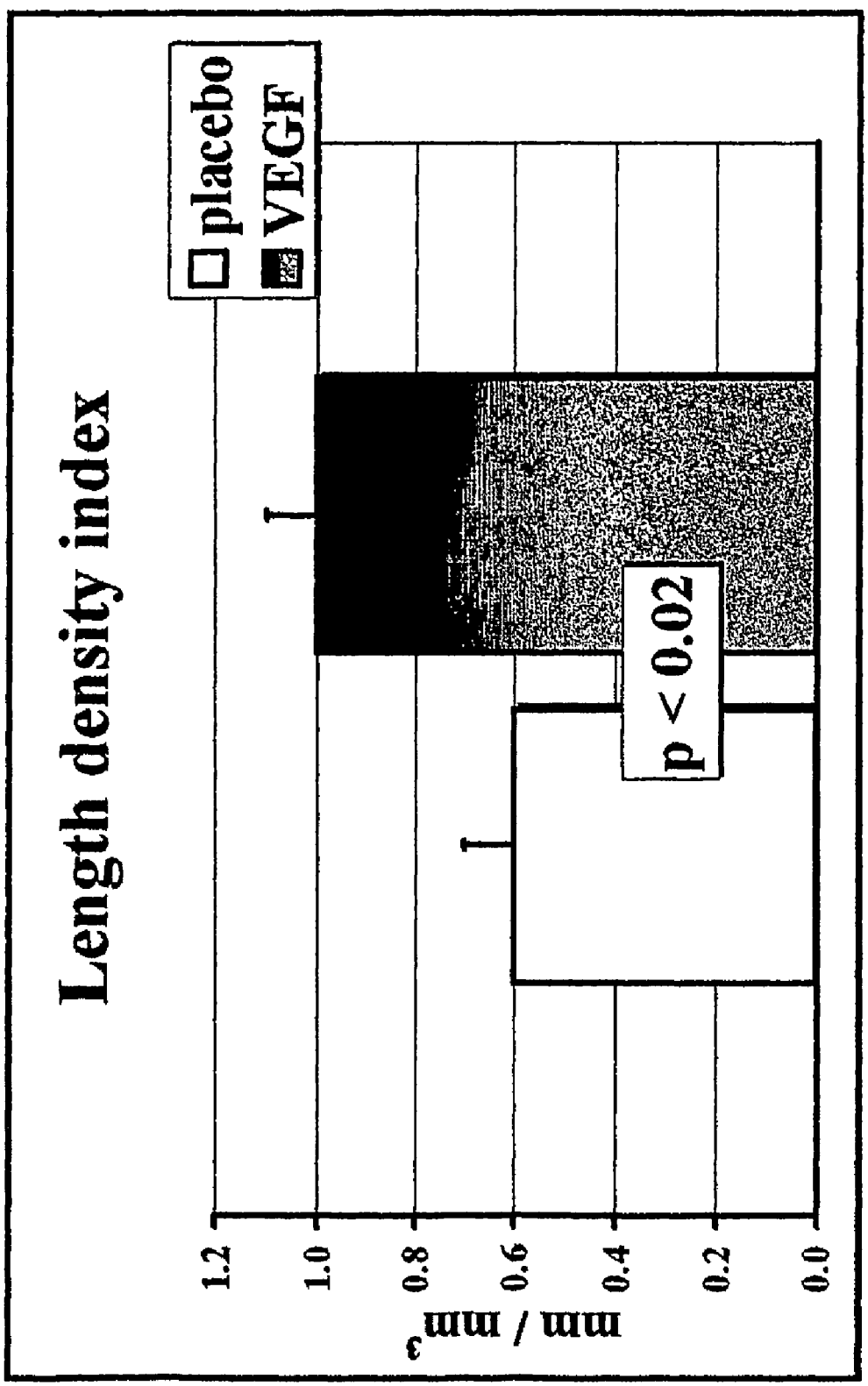
FIG. 5 shows the length density for the area under risk. Mean values for blood vessels with smooth muscle layer ranging from 8 to 30 μm are illustrated. The value for Group I-T (VEGF) is significantly higher than the value for Group I-P (placebo).
Figure 6:
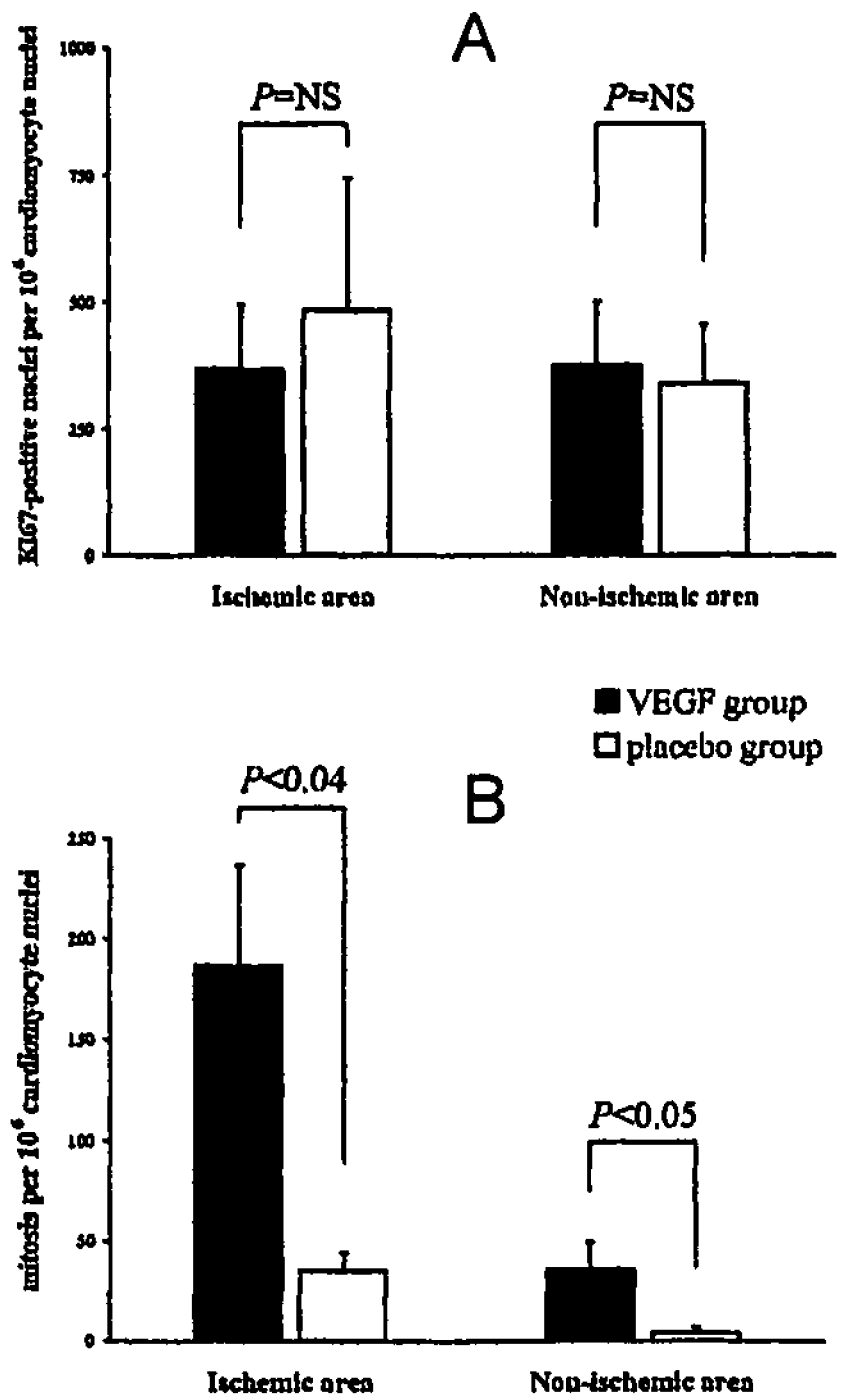
FIG. 6 illustrates the effect of ischemia and treatment on cardiomyocyte Ki67-positive nuclei and mitosis.

The physiological study demonstrated an overall improvement in the perfusion and stress tolerance of Group I-T individuals when treated with pUVEK15. See Tables 1 and 2; FIGS. 1 and 2.

The histopathological study showed statistically significant differences in numerical density, length density and mitotic index between both subgroups (inter-group non-paired comparisons). The Group I-T individuals presented higher mean values for these indexes when compared to Group I-P individuals. See Tables 3, 4, 5 and 6; FIGS. 3, 4, 5, 6, 8, 9, 10, 11, 12 and 13.

These results confirmed neovascular formation in vivo of myocardial tissue in the individuals treated with pUVEK15. Vascular formation and growth implies an increase in the number of cells taking part of neovessels (endothelial and vascular smooth muscle cells). See FIGS. 12 and 13. The administration of the inducing agent enhanced mitosis of vascular cells in the individuals treated. The subgroup of individuals treated with pUVEK15 also showed a proportion of cardiomyocytes in mitotic process more than 5 times higher than the non-treated subgroup. See FIGS. 6, 8, 9, 10 and 11; Table 6.

Angiogenesis or other adverse side effects were not detected in the peripheral tissues of the individuals treated with pUVEK15.

2. Presence and Transcription of the VEGF Plasmid

Molecular studies showed presence of plasmid DNA in injected myocardial tissue of all Group II individuals (PCR technique). Plasmid DNA encoding for VEGF was found in the injected myocardial tissue of the Group II-T individuals. Placebo plasmid DNA was found in the injected myocardial tissue of the Group II-P individuals.

Figure 7:
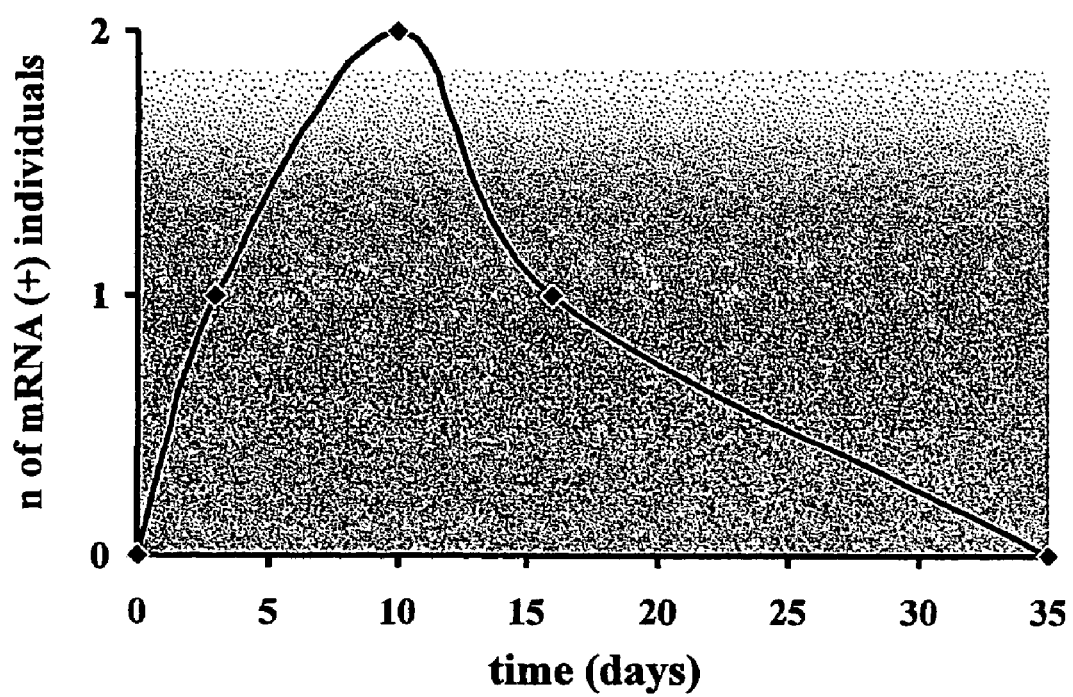
FIG. 7 represents the VEGF mRNA transcription curve of the Group II-T individuals. The curve shows a peak by day 10 post-injection of the pUVEK15 plasmid.
Figure 8:
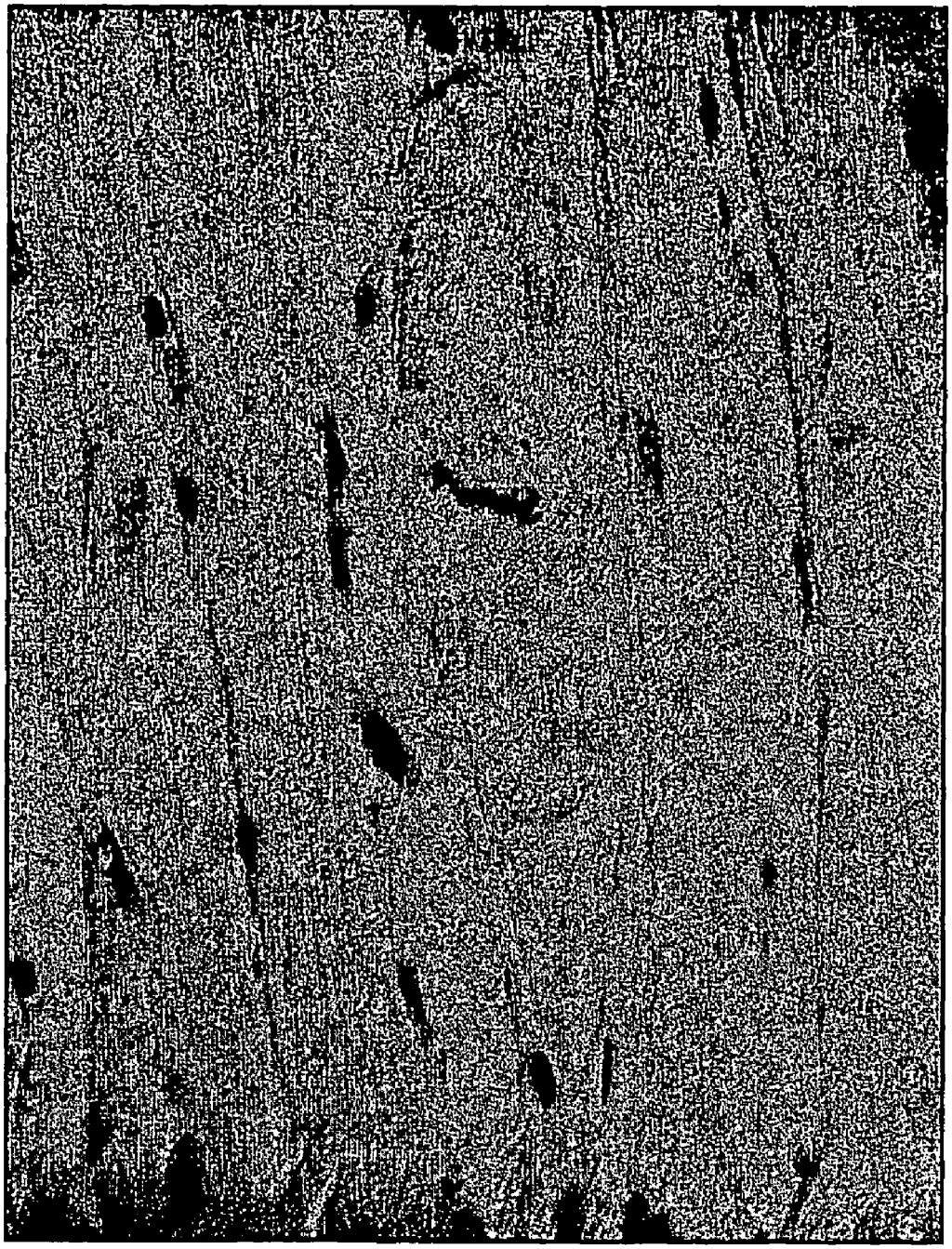
FIG. 8 illustrates the metaphase of a cardiomyocyte from a Group I-T individual. Metaphasic chromosomes and mitotic spindle are clearly visible.
Figure 9:
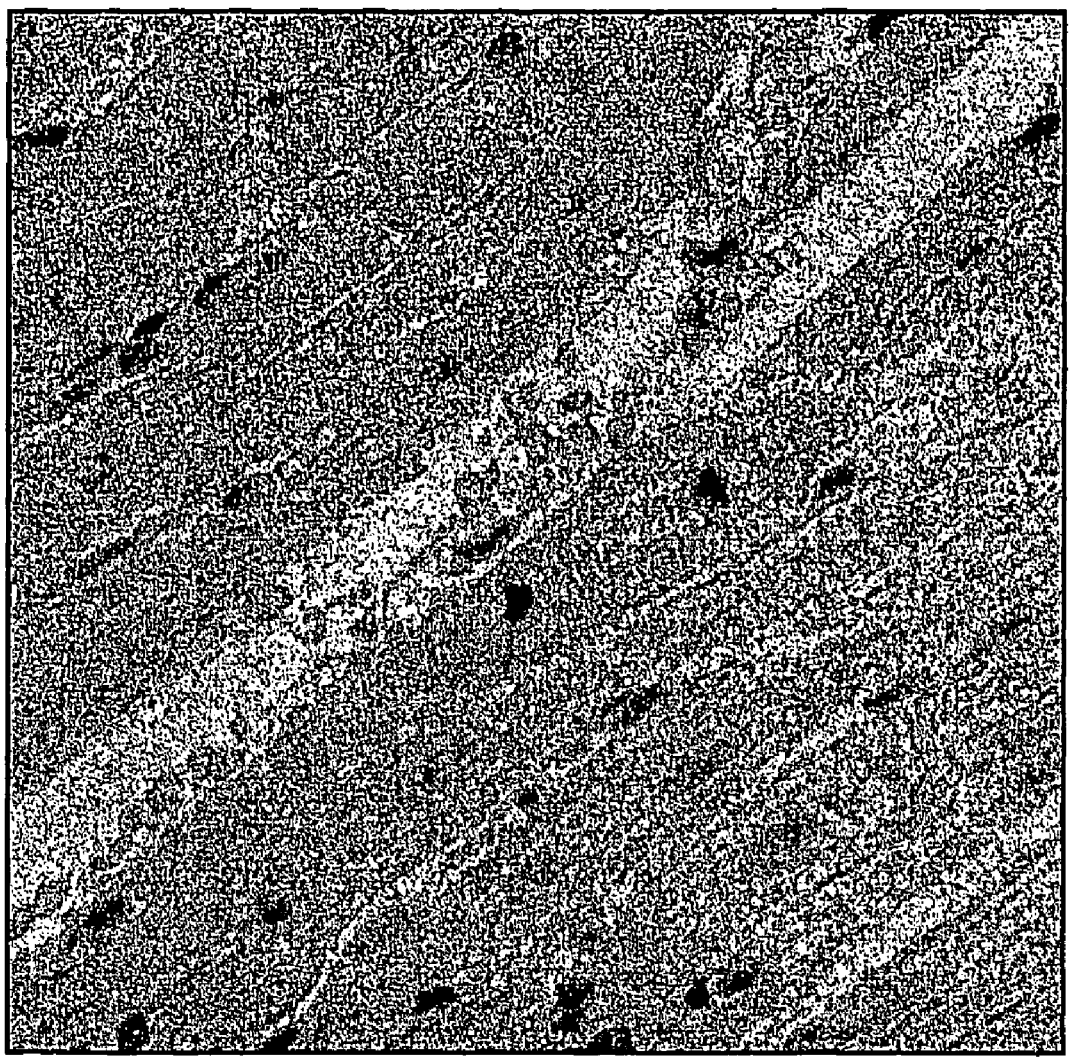
FIG. 9 illustrates the telophase of a cardiomyocyte from a Group I-T individual. Sarcomeric striations are clearly visible.
Figure 10:
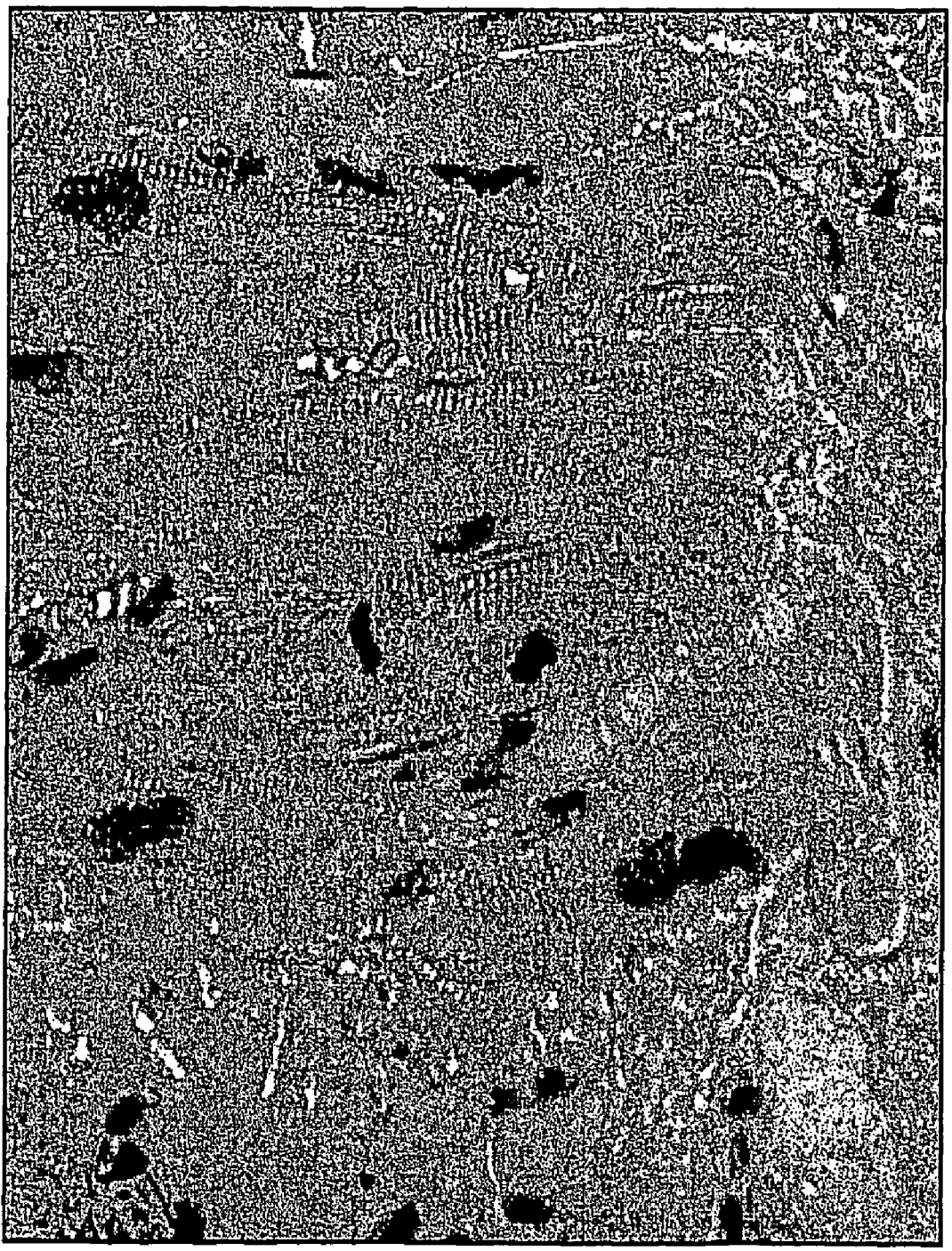
FIG. 10 illustrates the mitotic process of two adjacent cardiomyocytes. The boundary between the cardiomyocytes is distinguishable. The integrity of both cardiomyocytes is clearly observed.
Figure 11:
FIG. 11 shows the non-conventional cytokinesis of a cardiomyocyte from a Group I-T individual. Opposite chromosome plates in two adjacent cardiomyocytes are observed. The arrow indicates a possible splitting into daughter cells. Bar=10 μm.
Figure 12:
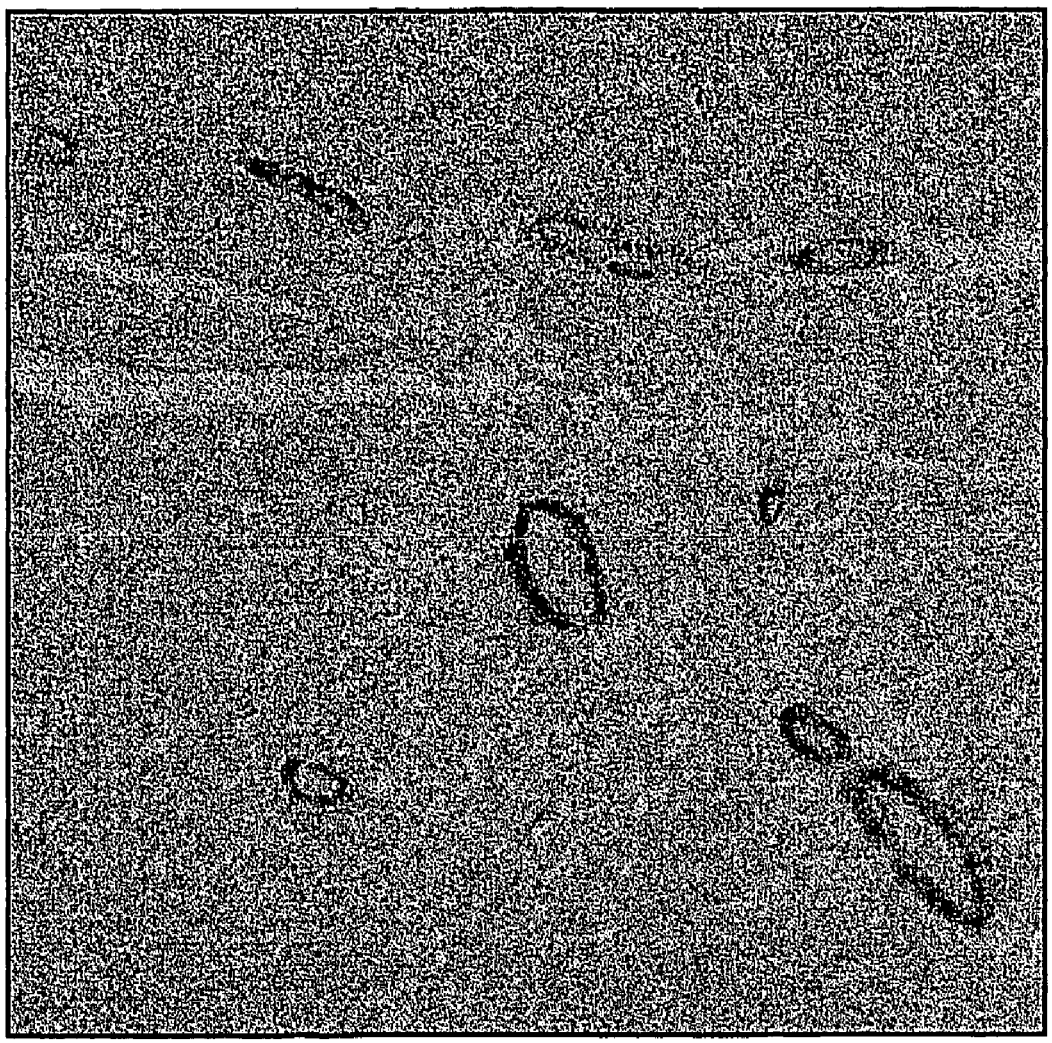
FIGS. 12 and 13 illustrate blood vessels with smooth muscle layer in myocardial tissue of a Group I-T individual. Vascular smooth muscle was identified with alpha-actin immunohistochemical stain.
Figure 13:

A positive RT-PCR product for pUVEK15 was detected in the injected myocardial tissue of the Group II-T individuals at 3 (n=1/2), 10 (n=2/2) and 16 (n=1/2) days post-treatment. See FIG. 7. No RT-PCR product for pUVEK15 was detected in inject myocardial tissue at 35 days (n=2) after pUVEK15 injection and in myocardial tissue receiving plasmid devoid of gene (Group II-P).

A transcription curve (presence of mRNA) showing a peak by day 10 post-injection of pUVEK15 was obtained in the Group II-T individuals. See FIG. 7. Presence of mRNA in group II-P was negative.

TABLE 1

| | Stress Tolerance Index | | | | |
|---|---|---|---|---|---|
| | Pre-treatment (1) | | Post-treatment (2) | | P value |
| | Mean | σ | Mean | σ | (1) vs (2) |
| Group I-P | −0.6 | 2.2 | −1.2 | 1.3 | 0.9 |
| Group I-T | −3.1 | 2.2 | 3.8 | 1.3 | <0.01 |
| P value I-T vs I-P | 0.42 | | <0.02 | | |

TABLE 2

| | Perfusion Improvement Index | |
|---|---|---|
| | Mean | σ |
| Group I-P | −0.6 | 2.6 |
| Group I-T | 6.9 | 2.6 |
| P value I-T vs I-P | 0.058 | |

TABLE 3

| | Numerical Density Index (8–50 μm) | |
|---|---|---|
| | Mean | σ |
| Group I-T | 1 | 0.1 |
| Group I-P | 0.6 | 0.1 |
| P Value I-T vs I-P | <0.02 | |

TABLE 4

| | Length Density Index (8–50 μm) | |
|---|---|---|
| | Mean | σ |
| Group I-T | 2.4 | 0.4 |
| Group I-P | 1.3 | 0.3 |
| P Value I-T vs I-P | <0.02 | |

TABLE 5

| | Length Density Index (8–30 μm) | |
|---|---|---|
| | Mean | σ |
| Group I-T | 1 | 0.1 |
| Group I-P | 0.6 | 0.1 |
| P Value I-T vs I-P | <0.02 | |

TABLE 6

| | Mitotic Index | |
| --- | --- | --- |
| | Mean | σ |
| Group I-T | 187.1 | 49.6 |
| Group I-P | 35.4 | 9.1 |
| P Value I-T vs I-P | <0.04 | |

Plasmids as above have also been introduced into sheep suffering from acute myocardial infarction, and myocardiogenesis has been observed. The methods in this study were adapted from the methods used in the preceding Examples.

REFERENCES

The following references are referred to in abbreviated bibliographic form above.

Senger D R, Galli S J, Dvorak A M, Perruzzi C A, Harvey V S, Dvorak H F. Tumor cells secrete a vascular permeability factor that promotes accumulation of ascites fluid. Science. 1983 Feb. 25, 1983; 219(4587):983-5.

Leung D W, Cachianes G, Kuang W J, Goeddel D V, Ferrara N. Vascular endothelial growth factor is a secreted angiogenic mitogen. Science. 1989 Dec. 8; 246(4935): 1306-9.

Vincenti V, Cassano C, Rocchi M, Persico G. Assignment of the vascular endothelial growth factor gene to human chromosome 6p21.3. Circulation. 1996 Apr. 15; 93(8): 1493-5.

Houck K A, Ferrara N, Winer J, Cachianes G, Li B, Leung D W. The vascular endothelial growth factor family: identification of a fourth molecular species and characterization of alternative splicing of RNA. Mol Endocrinol. 1991 December; 5(12):1806-14.

Tischer E, Mitchell R, Hartman T, Silva M, Gospodarowicz D, Fiddes J C, Abraham J A. The human gene for vascular endothelial growth factor. Multiple protein forms are encoded through alternative exon splicing. J Biol Chem. 1991 Jun. 25; 266(18): 11947-54.

Robinson C J, Stringer S E. The splice variants of vascular endothelial growth factor (VEGF) and their receptors. J Cell Sci. 2001 March; 114(Pt 5):853-65.

Muller Y A, Christinger H W, Keyt B A, de Vos A M. The crystal structure of vascular endothelial growth factor (VEGF) refined to 1.93 A resolution: multiple copy flexibility and receptor binding. Structure. 1997 Oct. 15; 5(10): 1325-38.

McDonald N Q, Hendrickson W A. A structural superfamily of growth factors containing a cystine knot motif. Cell. 1993 May 7; 73(3):421-4.

Murray-Rust J, McDonald N Q, Blundell T L, Hosang M, Oefner C, Winkler F, Bradshaw R A. Topological similarities in TGF-beta 2, PDGF-BB and NGF define a superfamily of polypeptide growth factors. Structure. 1993 Oct. 15; 1(2):153-9.

Sun P D, Davies D R. The cystine-knot growth-factor superfamily. Annu Rev Biophys Biomol Struct. 1995; 24:269-91.

Wiesmann C, Fuh G, Christinger H W, Eigenbrot C, Wells J A, de Vos A M. Crystal structure at 1.7 A resolution of VEGF in complex with domain 2 of the Flt-1 receptor. Cell. 1997 Nov. 28; 91(5):695-704.

Fairbrother W J, Champe M A, Christinger H W, Keyt B A, Starovasnik M A. Solution structure of the heparin-binding domain of vascular endothelial growth factor. Structure. 1998 May 15; 6(5):637-48.

Pötgens A J, Lubsen N H, van Altena M C, Vermeulen R, Bakker A, Schoenmakers J G, Ruiter D J, de Waal R M. Covalent dimerization of vascular permeability factor/vascular endothelial growth factor is essential for its biological activity. Evidence from Cys to Ser mutations. J Biol Chem. 1994 Dec. 30; 269(52):32879-85.

Keck P J, Hauser S D, Krivi G, Sanzo K, Warren T, Feder J, Connolly D T. Vascular permeability factor, an endothelial cell mitogen related to PDGF. Science. 1989 Dec. 8; 246 (4935):1309-12.

Siemeister G (a), Marme D, Martiny-Baron G. The alpha-helical domain near the amino terminus is essential for dimerization of vascular endothelial growth factor. J Biol Chem. 1998 May 1; 273(18):11115-20.

Peretz D, Gitay-Goren H, Safran M, Kimmel N, Gospodarowicz D, Neufeld G. Glycosylation of vascular endothelial growth factor is not required for its mitogenic activity. Biochem Biophys Res Commun. 1992 Feb. 14; 182(3): 1340-7.

Claffey K P, Senger D R, Spiegelman B M. Structural requirements for dimerization, glycosylation, secretion, and biological function of VPF/VEGF. Biochim Biophys Acta. 1995 Jan. 5; 1246(1):1-9.

Ferrara N, Davis-Smyth T. The biology of vascular endothelial growth factor. Endocr Rev. 1997 February; 18(1):4-25.

Keyt B A, Nguyen H V, Berleau L T, Duarte C M, Park J, Chen H, Ferrara N. Identification of vascular endothelial growth factor determinants for binding KDR and FLT-1 receptors. Generation of receptor-selective VEGF variants by site-directed mutagenesis. J Biol Chem. 1996 Mar. 8; 271(10): 5638-46.

Siemeister G (b), Schimer M, Reusch P, Barleon B, Marme D, Martiny-Baron G. An antagonistic vascular endothelial growth factor (VEGF) variant inhibits VEGF-stimulated receptor autophosphorylation and proliferation of human endothelial cells. Proc Natl Acad Sci USA. 1998 Apr. 14; 95(8):4625-9.

Houck K A, Leung D W, Rowland A M, Winer J, Ferrara N. Dual regulation of vascular endothelial growth factor bioavailability by genetic and proteolytic mechanisms. J Biol Chem. 1992 Dec. 25; 267(36):26031-7.

Plouet J, Moro F, Bertagnolli S, Coldeboeuf N, Mazarguil H, Clamens S, Bayard F. Extracellular cleavage of the vascular endothelial growth factor 189-amino acid form by urokinase is required for its mitogenic effect. J Biol Chem. 1997 May 16; 272(20): 13390-6.

Keyt B A (b), Berleau L T, Nguyen H V, Chen H, Heinsohn H, Vandlen R, Ferrara N. The carboxyl-terminal domain (111-165) of vascular endothelial growth factor is critical for its mitogenic potency. J Biol Chem. 1996 Mar. 29; 271(13): 7788-95.

Hirschi K K, Rohovski S A, D'Amore P A. PDGF, TGF-beta, and heterotypic cell-cell interactions mediate endothelial cell-induced recruitment of 10T1/2 cells and their differentiation to a smooth muscle fate. J. Cell. Biol. 1998; 141:805-814. [Erratum in J. Cell. Biol. 1998; 141:1287].

Jonca F, Ortega N, Gleizes P E, Bertrand N, Plouet J. Cell release of bioactive fibroblast growth factor 2 by exon 6-encoded sequence of vascular endothelial growth factor. J Biol Chem. 1997 Sep. 26; 272(39):24203-9.

Deposit

Plasmid pUVEK15 was deposited on Nov. 13, 2000, under access number DSM 13833 at the DSMZ—Deutsche Sammlung von Mikroorganismen und Zellkulturen, Mascheroder Weg 1B, D-38124 Braunschweig, Federal Republic of Germany.

The present invention has been described in some detail and exemplified to facilitate its understanding and reproducibility. Certain changes in the form and detail can be made by anyone skilled in the art without departing from the true object and scope of the claims of the present invention. The disclosure of all applications, patents and publication cited above and in the figures are hereby incorporated by reference in their entirety.

SEQUENCE LISTING

```
<160> NUMBER OF SEQ ID NOS: 4

<210> SEQ ID NO 1
<211> LENGTH: 165
<212> TYPE: PRT
<213> ORGANISM: Homo sapiens

<400> SEQUENCE: 1

Ala Pro Met Ala Glu Gly Gly Gly Gln Asn His His Glu Val Val Lys
 1               5                  10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
        50                  55                  60

Gly Leu Glu Cys Val Pro Thr Glu Glu Ser Asn Ile Thr Met Gln Ile
 65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
                100                 105                 110

Gln Glu Asn Pro Cys Gly Pro Cys Ser Glu Arg Arg Lys His Leu Phe
            115                 120                 125

Val Gln Asp Pro Gln Thr Cys Lys Cys Ser Cys Lys Asn Thr Asp Ser
        130                 135                 140

Arg Cys Lys Ala Arg Gln Leu Glu Leu Asn Glu Arg Thr Cys Arg Cys
145                 150                 155                 160

Asp Lys Pro Arg Arg
                165

<210> SEQ ID NO 2
<211> LENGTH: 576
<212> TYPE: DNA
<213> ORGANISM: Homo sapiens
<220> FEATURE:
<221> NAME/KEY: CDS
<222> LOCATION: (79)..(573)

<400> SEQUENCE: 2
atgaactttc tgctgtcttg ggtgcattgg agcctcgcct tgctgctcta cctccaccat          60
gccaagtggt cccaggct gca ccc atg gca gaa gga gga ggg cag aat cat         111
                    Ala Pro Met Ala Glu Gly Gly Gly Gln Asn His
                     1               5                  10
```

```
cac gaa gtg gtg aag ttc atg gat gtc tat cag cgc agc tac tgc cat    159
His Glu Val Val Lys Phe Met Asp Val Tyr Gln Arg Ser Tyr Cys His
            15                  20                  25 cca atc gag acc ctg gtg gac atc ttc cag gag tac cct gat gag atc    207
Pro Ile Glu Thr Leu Val Asp Ile Phe Gln Glu Tyr Pro Asp Glu Ile
            30                  35                  40 gag tac atc ttc aag cca tcc tgt gtg ccc ctg atg cga tgc ggg ggc    255
Glu Tyr Ile Phe Lys Pro Ser Cys Val Pro Leu Met Arg Cys Gly Gly
            45                  50                  55 tgc tgc aat gac gag ggc ctg gag tgt gtg ccc act gag gag tcc aac    303
Cys Cys Asn Asp Glu Gly Leu Glu Cys Val Pro Thr Glu Glu Ser Asn
 60             65                  70                  75 atc acc atg cag att atg cgg atc aaa cct cac caa ggc cag cac ata    351
Ile Thr Met Gln Ile Met Arg Ile Lys Pro His Gln Gly Gln His Ile
            80                  85                  90 gga gag atg agc ttc cta cag cac aac aaa tgt gaa tgc aga cca aag    399
Gly Glu Met Ser Phe Leu Gln His Asn Lys Cys Glu Cys Arg Pro Lys
            95                  100                 105 aaa gat aga gca aga caa gaa aat ccc tgt ggg cct tgc tca gag cgg    447
Lys Asp Arg Ala Arg Gln Glu Asn Pro Cys Gly Pro Cys Ser Glu Arg
            110                 115                 120 aga aag cat ttg ttt gta caa gat ccg cag acg tgt aaa tgt tcc tgc    495
Arg Lys His Leu Phe Val Gln Asp Pro Gln Thr Cys Lys Cys Ser Cys
            125                 130                 135 aaa aac aca gac tcg cgt tgc aag gcg agg cag ctt gag tta aac gaa    543
Lys Asn Thr Asp Ser Arg Cys Lys Ala Arg Gln Leu Glu Leu Asn Glu
140             145                 150                 155 cgt act tgc aga tgt gac aag ccg agg cgg tga                        576
Arg Thr Cys Arg Cys Asp Lys Pro Arg Arg
            160                 165

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caacatcacc atgcagatt                                               19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcaggaattc atcgattca                                               19
```

What is claimed is:

1. A method for inducing cardiomyogenesis in a subject in need of such treatment, comprising administering directly to a cardiomyocyte or tissue comprising cardiomyocytes in the subject a dose of a polynucleotide that encodes the vascular endothelial growth factor, VEGF1-165, wherein the coding sequence is operably linked to a CMV promoter and is in a plasmid vector, the dose being in a sufficient amount, which is greater than about 0.04 mg/kg, to induce cardiomyogenesis.

2. The method of claim 1, wherein the VEGF1-165 has the amino acid sequence:

Ala Pro Met Ala Glu Gly Gly Gly Gln    (SEQ ID NO: 1)

Asn His His Glu Val Val Lys Phe Met

Asp Val Tyr Gln Arg Ser Tyr Cys His

```
                        -continued

Pro Ile Glu Thr Leu Val Asp Ile Phe

Gln Glu Tyr Pro Asp Glu Ile Glu Tyr

Ile Phe Lys Pro Ser Cys Val Pro Leu

Met Arg Cys Gly Gly Cys Cys Asn Asp

Glu Gly Leu Glu Cys Val Pro Thr Glu

Glu Ser Asn Ile Thr Met Gln Ile Met

Arg Ile Lys Pro His Gln Gly Gln His

Ile Gly Glu Met Ser Phe Leu Gln His

Asn Lys Cys Glu Cys Arg Pro Lys Lys

Asp Arg Ala Arg Gln Glu Asn Pro Cys

Gly Pro Cys Ser Glu Arg Arg Lys His

Leu Phe Val Gln Asp Pro Gln Thr Cys

Lys Cys Ser Cys Lys Asn Thr Asp Ser

Arg Cys Lys Ala Arg Gln Leu Glu Leu

Asn Glu Arg Thr Cys Arg Cys Asp Lys

Pro Arg Arg.
```

3. The method of claim 1, wherein the induced cardiomyogenesis is localized.

4. The method of claim 1, wherein the cardiomyogenesis is induced in normoperfused tissue.

5. The method of claim 1, wherein the cardiomyogenesis is induced in ischemic tissue.

6. The method of claim 1, wherein the cardiomyogenesis is induced in myocardial tissue.

7. The method of claim 1, wherein the cell or tissue is eukaryotic.

8. The method of claim 1, wherein the cell or tissue is mammalian.

9. The method of claim 1, wherein the cell or tissue is porcine or human.

10. The method of claim 1, wherein the cell or tissue is human.

11. The method of claim 1, wherein the polynucleotide is a genomic DNA, a cDNA, or a messenger RNA.

12. The method of claim 11, wherein the polynucleotide encodes the polypeptide represented by SEQ ID NO: 1.

13. The method of claim 12, wherein the polynucleotide is a cDNA.

14. The method of claim 1, wherein the polynucleotide is administered to the cell or tissue in a liposome.

15. The method of claim 1, wherein the subject exhibits signs or symptoms of, or suffers from, ischemic heart disease, myocardial infarction, myocardial ischemia, dilated cardiomyopathy, or heart failure.

16. The method of claim 1, wherein the subject is a human patient.

17. The method of claim 1, wherein the polynucleotide is in the form of a pharmaceutical composition.

18. The method of claim 1, wherein the administration is intramuscular and is intramyocardial muscle administration.

19. The method of claim 18, wherein the administration is transepicardial or transendocardial administration.

20. The method of claim 19, wherein the administration is intramyocardial-transepicardial injection under direct visualization, or intramyocardial-transendocardial injection under fluoroscopic guidance.

21. The method of claim 18, wherein the polynucleotide is administered by injection perpendicular to the plane of the area of injection.

22. The method of claim 18, wherein the polynucleotide is administered by injection parallel to the plane of the area of injection.

23. The method of claim 18, wherein the polynucleotide is administered by injection at an oblique angle in relation to the plane of the area of injection.

24. The method of claim 23, wherein the angle in relation to the plane of the area of injection is between about 30° and about 90°.

25. The method of claim 18, wherein the polynucleotide is administered by injections that are homogeneously or heterogeneously distributed in the area of injection.

26. The method of claim 1, wherein the polynucleotide is administered in a single dose of between about 0.01 and about 0.36 nmoles /kg, wherein the nmoles are of the polynucleotide encoding the VEGF polypeptide.

27. The method of claim 26, wherein the polynucleotide is administered in a single dose of about between about 0.01 and about 0.10 nmoles/kg.

28. The method of claim 26, wherein the polynucleotide is administered in two or more doses, to achieve a total dose of between about 0.01 and about 0.36 nmoles /kg.

29. The method of claim 28, wherein the polynucleotide is administered in two or more doses, to achieve a total dose of between about 0.01 and about 0.10 nmoles/kg.

30. The method of claim 1, wherein the concentration of the plasmid vector is between about 0.5 and about 4 mg/mL.

31. A method for inducing mitosis or proliferation of a cardiomyocyte in a subject in need of such treatment, comprising administering directly to the cardiomyocyte cell a dose of a polynucleotide that encodes the vascular endothelial growth factor, VEGF 1-165, wherein the coding sequence is operably linked to a CMV promoter and is in a plasmid vector, the dose being in a sufficient amount, which is greater than about 0.04 mg/kg, to induce the mitosis or proliferation.

32. The method of claim 31, wherein the VEGF1-165 has the amino acid sequence:

```
Ala Pro Met Ala Glu Gly Gly Gly Gln  (SEQ ID NO: 1)

Asn His His Glu Val Val Lys Phe Met

Asp Val Tyr Gln Arg Ser Tyr Cys His

Pro Ile Glu Thr Leu Val Asp Ile Phe

Gln Glu Tyr Pro Asp Glu Ile Glu Tyr

Ile Phe Lys Pro Ser Cys Val Pro Leu

Met Arg Cys Gly Gly Cys Cys Asn Asp

Glu Gly Leu Glu Cys Val Pro Thr Glu

Glu Ser Asn Ile Thr Met Gln Ile Met

Arg Ile Lys Pro His Gln Gly Gln His

Ile Gly Glu Met Ser Phe Leu Gln His

Asn Lys Cys Glu Cys Arg Pro Lys Lys

Asp Arg Ala Arg Gln Glu Asn Pro Cys
```

-continued

```
Gly Pro Cys Ser Glu Arg Arg Lys His

Leu Phe Val Gln Asp Pro Gln Thr Cys

Lys Cys Ser Cys Lys Asn Thr Asp Ser

Arg Cys Lys Ala Arg Gln Leu Glu Leu

Asn Glu Arg Thr Cys Arg Cys Asp Lys

Pro Arg Arg.
```

33. The method of claim 31, wherein the cardiomyocyte is in a cardiac tissue.

34. The method of claim 33, wherein the cell or tissue is eukaryotic.

35. The method of claim 33, wherein the mitosis or proliferation is localized mitosis or proliferation.

36. The method of claim 33, wherein the mitosis or proliferation induces tissue regeneration.

37. The method of claim 33, wherein the tissue is normoperfused tissue.

38. The method of claim 33, wherein the tissue is ischemic tissue.

39. The method of claim 33, wherein the tissue is myocardial tissue.

40. The method of claim 33, wherein the tissue is hypoperfused tissue.

41. The method of claim 26, wherein the polynucleotide is administered in a single dose of greater than about 0.04 mg/kg.

42. The method of claim 41, wherein the polynucleotide is administered in two or more doses, to achieve a total dose of greater than about 0.04 mg/kg.

43. The method of claim 1, which is a method to reduce infarct size.

44. The method of claim 1, wherein the cardiomyogenesis is induced in hypoperfused tissue.

45. The method of claim 1, further wherein arteriogenesis is induced.

* * * * *

UNITED STATES PATENT AND TRADEMARK OFFICE
CERTIFICATE OF CORRECTION

PATENT NO. : 7,563,777 B2  Page 1 of 1
APPLICATION NO. : 10/714449
DATED : July 21, 2009
INVENTOR(S) : Laguens et al.

It is certified that error appears in the above-identified patent and that said Letters Patent is hereby corrected as shown below:

In Claim 18, column 31, line 64, delete "intramuscular and is".

Signed and Sealed this

Fifteenth Day of September, 2009

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,563,777 B2 |
| APPLICATION NO. | : 10/714449 |
| DATED | : July 21, 2009 |
| INVENTOR(S) | : Laguens et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 854 days.

Signed and Sealed this
Thirtieth Day of April, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,563,777 B2 | Page 1 of 1 |
| APPLICATION NO. | : 10/714449 | |
| DATED | : July 21, 2009 | |
| INVENTOR(S) | : Laguens et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 980 days.

Signed and Sealed this
Eleventh Day of November, 2014

Michelle K. Lee
*Deputy Director of the United States Patent and Trademark Office*